US008877507B2

(12) United States Patent
Xia et al.

(10) Patent No.: US 8,877,507 B2
(45) Date of Patent: Nov. 4, 2014

(54) ENSURING SAMPLE ADEQUACY USING TURBIDITY LIGHT SCATTERING TECHNIQUES

(75) Inventors: Jiulin Xia, Germantown, MD (US); Richard L. Mantefuel, Laytonsville, MD (US); Carl Theodore Edens, Highland, MD (US); Jonathan Matthew Miller, Burke, VA (US); Nadia P. Allen, Montgomery Village, MD (US)

(73) Assignee: Qiagen Gaithersburg, Inc., Gaithersburg, MD (US)

( * ) Notice: Subject to any disclaimer, the term of this patent is extended or adjusted under 35 U.S.C. 154(b) by 146 days.

(21) Appl. No.: 12/588,305

(22) Filed: Oct. 9, 2009

(65) Prior Publication Data

US 2010/0205139 A1 Aug. 12, 2010

Related U.S. Application Data

(63) Continuation-in-part of application No. 12/062,950, filed on Apr. 4, 2008, now Pat. No. 7,985,375.

(60) Provisional application No. 61/242,628, filed on Sep. 15, 2009, provisional application No. 61/183,857, filed on Jun. 3, 2009, provisional application No. 60/910,565, filed on Apr. 6, 2007.

(51) Int. Cl.
*G01N 21/51* (2006.01)
*G01N 35/00* (2006.01)
*B01L 9/06* (2006.01)
*G01N 21/03* (2006.01)
*G01N 15/06* (2006.01)

(52) U.S. Cl.
CPC ............ *B01L 9/06* (2013.01); *G01N 35/00594* (2013.01); *G01N 2035/00524* (2013.01); *G01N 2015/0693* (2013.01); *B01L 2200/025* (2013.01); *G01N 21/51* (2013.01); *B01L 2300/0829* (2013.01); *G01N 35/0099* (2013.01); *G01N 2035/00534* (2013.01)
USPC ............. 436/43; 356/339; 356/237.1; 706/54

(58) Field of Classification Search
None
See application file for complete search history.

(56) References Cited

U.S. PATENT DOCUMENTS 3,013,466 A 12/1961 Kaye
3,713,743 A 1/1973 Simms
(Continued)

FOREIGN PATENT DOCUMENTS

EP 0127418 A2 12/1984
EP 193868 A2 9/1986
(Continued)

OTHER PUBLICATIONS

International Search Report from PCT/US09/064258 mailed Jan. 6, 2010.
(Continued)

*Primary Examiner* — Yelena G Gakh
*Assistant Examiner* — Michelle Adams
(74) *Attorney, Agent, or Firm* — RatnerPrestia

(57) ABSTRACT

An automated method for assuring sample adequacy. The method includes providing a sample in a testing container, activating an illumination source to pass an illumination beam through the testing container and into the sample, and detecting an intensity of an emitted beam. The emitted beam includes at least a portion of the illumination beam that has been scattered by the sample. The method also includes generating a sample turbidity measurement based on the intensity of the emitted beam, and determining, based on the sample turbidity measurement, an adequacy of the sample to provide accurate results in a primary test.

17 Claims, 33 Drawing Sheets

(56) References Cited

U.S. PATENT DOCUMENTS

| | | |
|---|---|---|
| 3,744,665 A | 7/1973 | Spoto |
| 3,775,013 A | 11/1973 | Simms |
| 3,826,574 A | 7/1974 | Brown, Jr. |
| 3,832,532 A | 8/1974 | Praglin et al. |
| 4,152,070 A | 5/1979 | Kushner et al. |
| 4,169,125 A | 9/1979 | Rodriguez et al. |
| 4,343,552 A | 8/1982 | Blades |
| 4,363,551 A | 12/1982 | Achter et al. |
| 4,401,387 A | 8/1983 | Tokinage et al. |
| 4,448,534 A | 5/1984 | Wertz et al. |
| 4,477,190 A | 10/1984 | Liston et al. |
| 4,603,977 A | 8/1986 | Bennett et al. |
| 4,669,878 A | 6/1987 | Meier |
| 4,684,252 A | 8/1987 | Makiguchi et al. |
| 5,011,286 A * | 4/1991 | Petralli .................. 356/343 |
| 5,017,785 A | 5/1991 | Rasanen |
| 5,116,122 A | 5/1992 | Fukuma |
| 5,202,262 A | 4/1993 | Lemonnier |
| 5,422,483 A | 6/1995 | Ando et al. |
| 5,589,935 A * | 12/1996 | Biard ..................... 356/339 |
| 5,729,333 A | 3/1998 | Osten et al. |
| 5,817,025 A | 10/1998 | Alekseev et al. |
| 5,872,361 A | 2/1999 | Paoli et al. |
| 5,940,178 A | 8/1999 | Barber et al. |
| 5,963,318 A | 10/1999 | Held |
| 6,307,630 B1 | 10/2001 | Banerjee |
| 6,388,751 B1 | 5/2002 | Holley |
| 6,444,472 B1 | 9/2002 | Cohen et al. |
| 6,618,144 B1 * | 9/2003 | Reed ..................... 356/343 |
| 6,620,585 B1 | 9/2003 | Zyskind |
| 6,803,594 B2 | 10/2004 | Spolaczyk et al. |
| 6,844,934 B2 | 1/2005 | Retzlaff et al. |
| 6,894,778 B2 | 5/2005 | Palumbo et al. |
| 7,000,785 B2 | 2/2006 | Jafari et al. |
| 7,033,542 B2 | 4/2006 | Archibald et al. |
| 7,118,892 B2 | 10/2006 | Ammann et al. |
| 7,209,231 B2 | 4/2007 | Rastopov |
| 7,226,777 B2 | 6/2007 | Kawamura et al. |
| 7,339,668 B2 | 3/2008 | Ebersole et al. |
| 7,430,043 B1 | 9/2008 | Evans |
| 7,491,366 B2 | 2/2009 | Tokhtuev et al. |
| 2002/0086431 A1 | 7/2002 | Markham et al. |
| 2002/0090320 A1 | 7/2002 | Burow et al. |
| 2002/0125230 A1 | 9/2002 | Haight et al. |
| 2002/0186363 A1 | 12/2002 | Samsoondar et al. |
| 2003/0069699 A1 | 4/2003 | Ekins et al. |
| 2003/0169421 A1 | 9/2003 | Ehbets |
| 2004/0029135 A1 | 2/2004 | Ramberg |
| 2004/0076546 A1 | 4/2004 | Bissett |
| 2004/0209374 A1 | 10/2004 | Kopf-Sill et al. |
| 2004/0260157 A1 | 12/2004 | Montes |
| 2005/0069913 A1 | 3/2005 | Mian et al. |
| 2005/0070020 A1 | 3/2005 | Klautky et al. |
| 2005/0206895 A1 | 9/2005 | Salmelainen |
| 2005/0254055 A1 | 11/2005 | Peng |
| 2006/0103842 A1 | 5/2006 | Tokhtuev et al. |
| 2006/0136095 A1 | 6/2006 | Rob et al. |
| 2008/0030712 A1 | 2/2008 | Tokhtuev et al. |
| 2008/0160539 A1 | 7/2008 | Murphy et al. |
| 2008/0174768 A1 | 7/2008 | Belz |
| 2008/0247914 A1 | 10/2008 | Edens et al. |
| 2009/0098022 A1 | 4/2009 | Tokhtuev et al. |

FOREIGN PATENT DOCUMENTS

| | | |
|---|---|---|
| GB | 1013874 A | 12/1965 |
| GB | 1122809 A | 8/1968 |
| GB | 1128446 A | 9/1968 |
| GB | 1250594 A | 10/1971 |
| GB | 1486210 A | 9/1977 |
| GB | 2088580 A | 6/1982 |
| GB | 2248944 A | 4/1992 |
| GB | 2355524 A | 4/2001 |
| GB | 2431232 A | 4/2007 |
| JP | 55016258 A | 2/1980 |
| JP | 58099733 A | 6/1983 |
| JP | 60125541 A | 7/1985 |
| JP | 3189542 A | 8/1991 |
| JP | 5018885 A | 1/1993 |
| JP | 7253392 A | 10/1995 |
| JP | 10332582 A | 12/1998 |
| JP | 2006047166 A | 2/2006 |
| JP | 2006317269 A | 11/2006 |
| JP | 2006317220 A | 11/2006 |
| JP | 2008064594 A | 3/2008 |
| JP | 2008249363 A | 10/2008 |
| JP | 2008286659 A | 11/2008 |
| WO | WO 0129534 A1 | 4/2001 |
| WO | WO 2006052822 A2 | 5/2006 |
| WO | WO 2006116835 A1 | 11/2006 |
| WO | WO 2007/048042 | 4/2007 |
| WO | WO 2007060583 A2 | 5/2007 |
| WO | WO 2008035864 A1 | 3/2008 |
| WO | WO 2009061729 A1 | 5/2009 |

OTHER PUBLICATIONS

International Search Report from PCT/US09/64244 mailed Jan. 26, 2010.

International Search Report from PCT/US09/64236 mailed Jan. 27, 2010.

International Search Report from PCT/US09/064268 mailed Mar. 10, 2010.

Examination Report for Australia Patent Application No. 2009347207 dated Dec. 4, 2013.

Office Action, with English translation, for Taiwan Patent Application No. 98138424 dated Jul. 28, 2014.

* cited by examiner

Fig. 7  Comparison between qPCR cell levels and Turbidity values (Vol:>4ml:N=669) & (Vol:>2ml,<4ml:N=23)

Fig. 9  Comparison of optical cell counting to qPCR: N=99

Fig. 10  Comparison of Optically counted cells to Turbidity values: N=99

Fig. 12 Comparison of Turbidity to Human Cell count in Positive clinical pool dilution series: N=28

Fig. 13  Comparison of qPCR to Human cell count in Positive Clinical Pool dilution series: N=28

Fig. 17 Comparison of PC_QNS (Vol >2ml <4ml) vs turbidity (N=172)

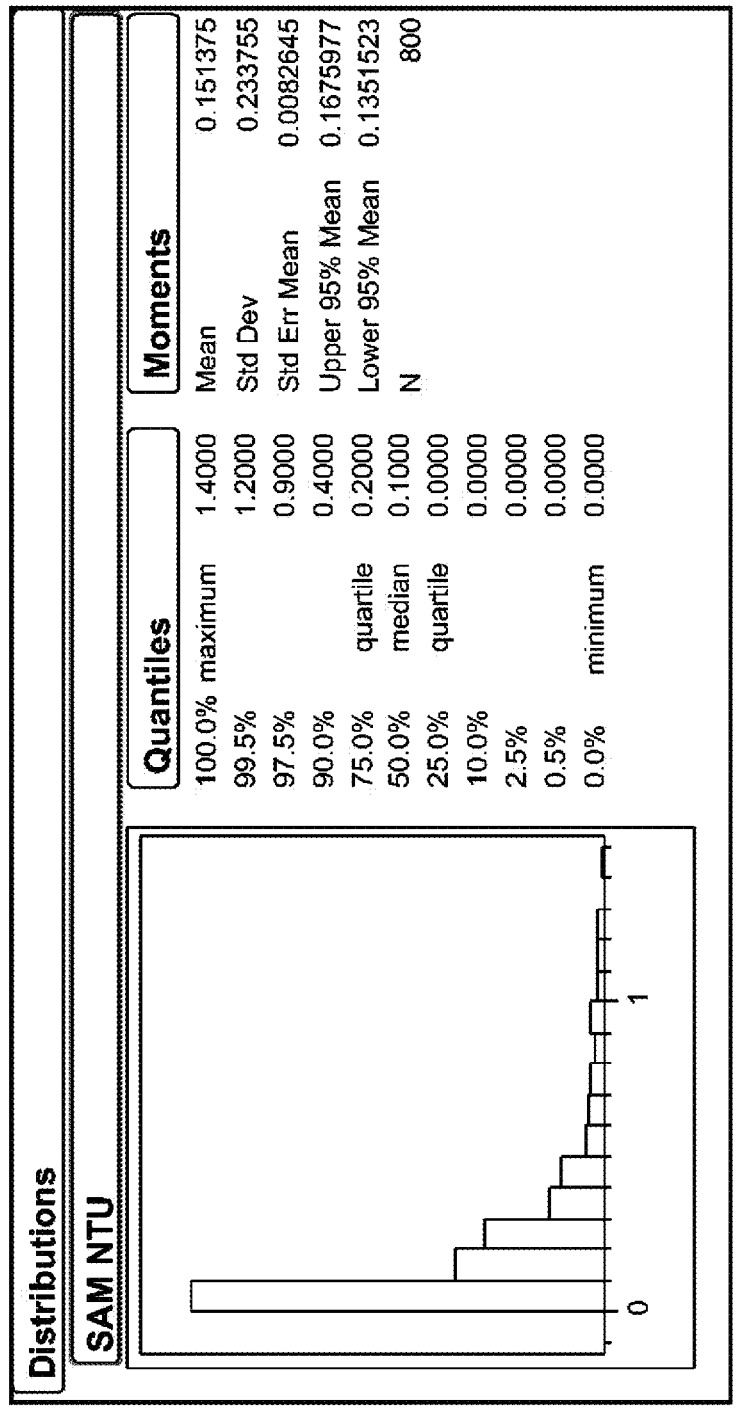
Fig. 33  Distribution of turbidity measurements of blank samples

ENSURING SAMPLE ADEQUACY USING TURBIDITY LIGHT SCATTERING TECHNIQUES

RELATED APPLICATION DISCLOSURE

This application claims the benefit of U.S. Provisional Application Ser. No. 61/242,628 filed Sep. 15, 2009 entitled "Ensuring Sample Adequacy of Clinical Cervical Specimens Using Turbidity Light Scattering Techniques" and U.S. Provisional Application Ser. No. 61/183,857 filed Jun. 3, 2009 entitled "Ensuring Sample Adequacy of Clinical Cervical Specimens Using Turbidity Light Scattering Techniques" which are incorporated by reference herein in their entireties. This application is also a continuation-in-part of U.S. Ser. No. 12/062,950, filed Apr. 4, 2008 now U.S. Pat. No. 7,985,375, which claims the benefit of U.S. Provisional Application Ser. No. 60/910,565 filed Apr. 6, 2007, which are incorporated by reference herein in their entireties.

BACKGROUND

1. Field of the Art

This disclosure generally relates to methods of measuring the adequacy of a clinical sample by estimating the cell count in known fluid volumes using light scattering techniques, in particular turbidity. In another aspect, this disclosure provides machines for measuring the adequacy of a clinical sample by estimating the cell count. These machines can be used for high-throughput processing of clinical samples. In another aspect, this disclosure provides methods of determining whether testing of a clinical sample would be informative comprising determining whether the sample contains adequate material for test to be informative.

2. Description of Related Art

In the fields of Clinical Diagnostics, Life Sciences, Forensics, and BioDefense, assurance of a sample's adequacy determination can provide several benefits to the process of sample analysis. Information content about the sample's adequacy can increase confidence in and efficacy of subsequent test results using other chemical, physical, and/or biological assays on that sample. Information content improves patient treatment since patients whose health status would be misrepresented by inadequate sample are more likely to be discovered. Avoidance of reporting an unrepresentative health result and allowing for patient re-sampling are anticipated beneficial results of sample adequacy determination. Additionally, knowledge of the sample's adequacy prior to running other sample analysis can result in time, material, and labor savings by avoiding costly testing on un-vetted inadequate samples. Thus, establishing Sample Assurance in screening tests on large populations where a significant number of the test results confirm an absence of analyte can add value as a confirmation that the result is representative of the original entity sampled.

Clinical samples which are being analyzed for the presence of specific cell types, viruses, bacteria or other pathogens can particularly benefit from the subject test methods as these methods will facilitate the accuracy of the test results and further enhance efficiency. One specific area that can potentially benefit from sample adequacy assurance is testing of cervical samples for HPV infection. For example, the digene HC2 High-Risk HPV DNA Test® (HC2) has proven to be of extreme value as a component of cervical cancer screening programs and clinical management of ASC-US cytology patients. Currently HC2 HPV DNA testing yields a high negative predictive value of approximately 99.5% for prediction of cervical lesions of CIN3 or greater. Nonetheless, laboratories and patients may desire the additional control and assurance that would be provided by measurement of sample adequacy. The opportunity to decline to test a sample determined to be inadequate may also be desired.

SUMMARY

In view of the foregoing, there is a need for methods to determine sample adequacy. The use of these methods can allow an operator to determine whether to exclude processing of a sample that is deemed inadequate for specific testing methods. These methods can provide knowledge of sample adequacy, which may be useful for interpretation of test results and patient care decisions. For example, if a sample is inadequate, a negative result can be understood to not necessarily represent a true negative, though a positive result may still be considered informative for certain types of tests. Sample inadequacy determination can give the option of re-sampling to obtain an adequate sample prior to testing, thereby saving costs of performing a potentially indeterminate assay. Thus, the methods described herein can put greater decision making capability the user's hands, for example by allowing determination of whether to test an inadequate sample, and can provide the care provider and/or patient a better understanding of the meaning of a negative test result. Preferred embodiments of the invention may provide one or more of the foregoing benefits, but other benefits may be realized instead of or in addition to these.

The present disclosure provides a number of inventions that may be used collectively, in various combinations, or alone. The following summary provided examples of such inventions, and does not limit the invention as claimed in any way.

In one aspect, the present disclosure provides a sample assurance reader comprising one or more channels to measure turbidity of one or more samples in unison or separately, each comprising: one or more light sources and one or more light detectors, whereby a sample is determined to be adequate or inadequate for a primary test.

In another aspect, the present disclosure provides an automated system that is configurable through software, firmware or hardware such that it can discontinue processing of samples that have been identified as inadequate or un-assured.

In another aspect, the present disclosure provides a method of using a sample assurance reader to determine the turbidity of at least one sample prior to effecting at least one primary test, wherein the primary test is an HPV primary or secondary screening test.

In another aspect, the present disclosure provides a method of using a sample assurance reader to determine the turbidity of at least one sample prior to effecting at least one primary test, wherein the primary test is a viral infection screening test.

In another aspect, the present disclosure provides an automated system for conducting a primary test comprising a sample assurance determination module.

In another aspect, the present disclosure provides a sample container for use in an optical measurement system comprising at least one of a lens for controlling the beam's angle of illumination and a lens for controlling the path of emitted light.

In another aspect, the present disclosure provides a method of determining sample adequacy comprising: receiving, using a processor, data containing a measurement of turbidity of the sample; comparing, using a processor, the measurement of turbidly against one or more specified criteria stored in electronic storage; determining, using a processor, a sample adequacy result based at least in part on the comparison; and providing an indicator of the sample adequacy result.

In another aspect, the present disclosure provides a system for determining sample adequacy, comprising: a processor communicatively coupled to electronic storage wherein the processor is configured to: receive a measurement of turbidity of the sample; compare the measurement of turbidly against one or more specified criteria stored in electronic storage; determine a sample adequacy result based at least in part on the comparison; and provide an indicator of the sample adequacy result.

In another aspect, the present disclosure provides an automated system for transferring a sample between containers prior to conducting a primary test comprising a sample assurance determination module.

BRIEF DESCRIPTION OF THE DRAWINGS

FIG. 33 shows the distribution of turbidity measurements of blank samples by an 8-channel SAM.

DETAILED DESCRIPTION

Figure 1:
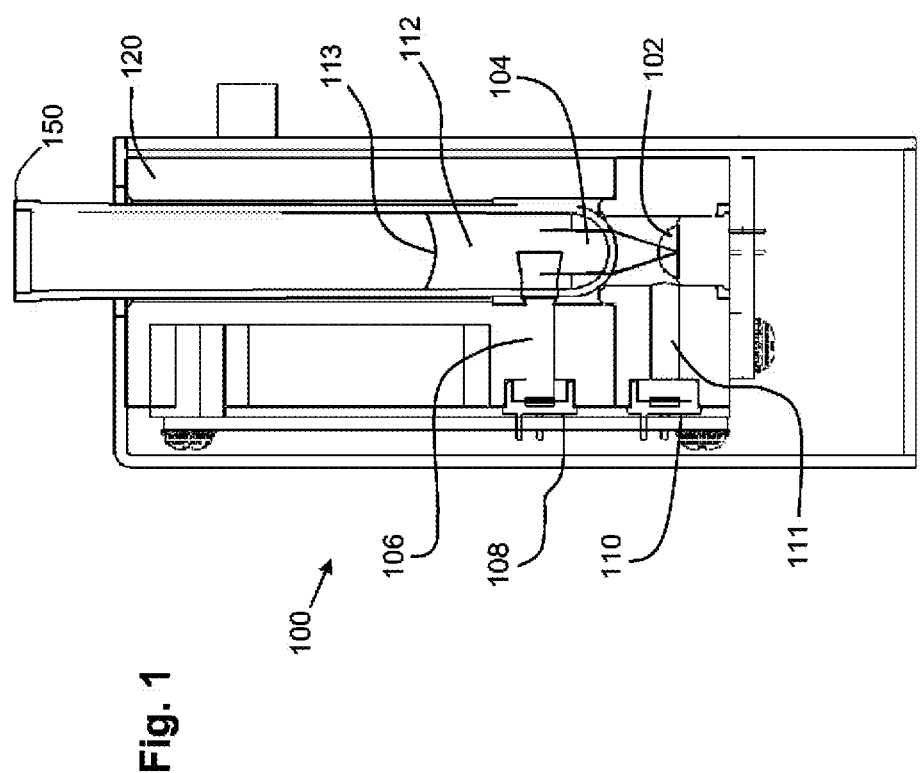
FIG. 1 generally comprises a Sample Adequacy Control Measurement System ("SAM").

The methods and devices described herein can be used to improve the quality of test results in many industries and applications and with many sample types. This includes by way of example male and female human tissue samples which are being assayed for the presence of specific abnormal cell types, viruses, bacteria and the like. Certain specific examples provided in this disclosure are related to the improvement of Women's Health by evaluating tissue samples for infection by one or more viral strains. Of specific interest in these examples is the analytical detection of multiple Human Papilloma Virus strains such as HPV 16, HPV 18, and HPV 45 which are high risk strains known to cause cervical cancer in women. The detection of the virus using existing methods generally use epithelial cells sampled by a brush/swab scrape of a female patient's cervix be suspended in a liquid media. The media properties generally prevent growth of vaginal bacteria or contaminants, provide stability to the epithelial cells and free virus, and allow for sample portioning for tests that permit detection of HPV or the consequences of HPV infection, which include histological examination, immunological assays, and DNA assays.

Improper sample acquisition or contamination may yield a negative result due to the absence of representative free HPV viral DNA or an absence of infected cells. Some HPV viral screening tests such as Hybrid Capture 2 from Qiagen Corporation can detect levels as low as 5000 copies of the virus. Some sample acquisition protocols allow for a cervical brush or swab to be used to scrap cells from the cervical area of a female patient by the health practitioner. The practitioner then immediately swirls the brush around in a new sample container filled by the factory with a transport media such as PreservCyt™ or SurePath™. The container is labeled closed and then sent to a lab for HPV screening. At this point the media and sample are combined and considered to be the same. Several forms of sample acquisition error or contamination could occur in the process. If the practitioner does not scrape the lining of the cervix with proper force or technique, they may not collect a representative number or epithelial cells on the brush/swab. The transfer of the cells from the brush/swab to the transport media may be poor resulting in fewer or no representative cervical cells transferring to the media. During collection contamination may occur. Contaminants such as dust, bacteria, particulates, DNA-ase, hair, mucus, etc could enter the sample container, media, or sample. Alternatively, an unused container of transport media may be mislabeled as the patients sample and sent to the lab. Such samples may be inadequate for testing. If the inadequate sample goes undetected then a negative result would be reported while the patient's actual health status has not actually been determined and thus remains unknown.

Upon receipt at the lab the inadequate sample would be transferred from the primary acquisition container and assayed to determine if HPV virus is present in the transport media. Some assays require homogenization of the fluid to some level while others do not. During transfer from the primary or subsequent containers an unrepresentative version of the sample may be obtained for the assay. For instance if the sample is clumping or settling in the sample container an aliquoted portion may misrepresent the sample. Methods of establishing sample assurance both non-destructively and while consuming minimal sample can be particularly beneficial because sample is considered precious since sample acquisition is often a cause of minor trauma to the patient and may be infrequent for a given patient. Preferred embodiments of the invention may provide one or more of the foregoing benefits, but other benefits may be realized instead of or in addition to these.

Inadequate samples are likely to yield a negative HPV result regardless of the patient's actual health status. qPCR based detection systems such as those distributed by Roche and ThirdWave offer an internal control that allows confirmation of DNA amplification during the analyte detection test. Specifically, these tests amplify and detect Beta-Globin a strand of DNA found in Hemoglobin. Hemoglobin is prevalent in cervical tissue scrape samples. Quantifying the Beta-Globin levels present increases sample assurance. Beta-Globin is used to approximate the number of cells per milliliter of sample media present though it is not a direct count of epithelial cells. Other housekeeping genes such as Histone may also be used. Since the determination of Beta-Globin uses the same reagents as the analysis of the analyte it is run at the same time as the analyte test. As a result the confidence in test results increases but there is no potential savings in time, labor, or materials due to the post facto understanding of the sample's adequacy.

This disclosure provides methods to determine the adequacy of a sample prior to analyte determination in the form of a non-destructive blank differential control or cellularity control as described below. Where a blank differential control is a method of determining that there is physical property change between blank media and blank media combined with an adequate sample in this specific instance the physical difference is do to the cell density or cellularity of the combined sample and media.

In one aspect, this disclosure describes a device used to establish sample assurance (confidence in a sample's adequacy to be tested for a given clinical analyte to determine the health status of a patient). An exemplary device is shown to determine the sample adequacy of cervical tissue samples that are collected into a transport media or that have been concentrated and resuspended in a liquid media conducive to subsequent analyte or adequacy determination. These methods can be used as quality control for downstream diagnostic testing such as detecting the present of HPV virus in the same sample. It can also be used as a quality check prior to other molecular diagnostic testing such as Chlamydia, Gonorrhea, etc.

Exemplary embodiments can be used to analyze a sample prior to a DNA analysis assay, such as the Next Generation Hybrid Capture® High Risk assay developed by Qiagen GmbH of Hilden, Germany ("Qiagen"). Examples of this and other assays that can be performed in conjunction with sample adequacy determination by embodiments of the systems described herein are disclosed in U.S. Provisional Application Ser. No. 61/231,371, filed Aug. 5, 2009, entitled "METHODS AND KITS FOR ISOLATING NUCLEIC ACIDS USING AN ANION EXCHANGE MATRIX" and 61/147,862, filed Jan. 28, 2009, entitled "SEQUENCE SPECIFIC LARGE VOLUME SAMPLE PREP SOLUTION UTILIZING HYBRID CAPTURE TECHNOLOGY," which are incorporated herein by reference in their entireties.

While such a device may detect the sample adequacy before, during, or after detection of one or more analyte tests it is often beneficial to detect the adequacy of a sample earlier in the processing of the sample to allow for cost savings. Cost savings are more likely to be realized when a sample is determined as inadequate and downstream processing is halted on that sample. However, processing may be continued despite sample inadequacy, for example because a positive result (if obtained) may nonetheless be meaningful even if a sample is inadequate to provide confident interpretation of a negative result.

Exemplary methods of the present disclosure use light scattering technology similar to that used in turbidity meters to estimate the particulate level in a fluid. For example, in the field of environmental sciences the turbidity level of water sources as an estimate of the water quality is commonly determined with single channel turbidity meters. Turbidity levels are generally determined by illuminating a liquid sample with light and detecting the scattered light at an angle of incidence from the source illumination. The underlying physical principle is that particulate material in the liquid will absorb, reflect, refract, and diffract the light. Light shown on the liquid sample will either be absorbed or scattered beyond the angle of incidence of the illumination source. Generally, the more scattered (off-axis of illumination) light detected the more particulates in the fluid. Illumination wavelengths are selected that allow for the reflection of particulates of interest. In this case wavelengths that are generally reflected off of epithelial cells or free virus would be of interest because, without intent to be limited by theory, it is believed that for cervical and other similar samples, reflection off of cellular membranes is more likely to result in a detectable phenomena than reflection off of free virus.

The intensity of the illumination source determines the signal to noise ratio achievable for samples of a certain particulate density (cellularity). The higher the intensity the less absorbance will reduce the signal. It is preferred that the light is focused within the bulk liquid sample volume and away from the sample container surfaces to ensure the measurement of scatter is representative of the entire sample volume. Commercially available single channel turbidity meters, e.g., available from VWR and Hach, use broadband halogen light (halogen light bulb) and near infrared light emitting diodes (NIR LEDs) as primary illumination sources to assess turbidity. The use of a broadband source is a shotgun approach to ensuring that light scatter occurs but potentially sacrifices the signal to noise ratio thereby reducing the limit of detection and the resolution of the device. Additionally, broadband sources may waste energy relative to monochromatic sources to achieve the same signal level for a given particulate concentration in a liquid sample.

Preferably, control and measurement of the light intensity are utilized to reduce variability between scatter readings. For example, directly controlling the current to an illumination source (e.g. LED) in a closed loop system that is independently measuring the illumination intensity of the source can generate a constant illumination intensity. Similarly the intensity of the illumination source could simply be checked in a more open loop process to ensure it is in within an acceptable intensity range. A correction to the final detected scatter based on open loop intensity of the source light could also be applied in a pre-calibrated system to correct for variation in source light intensity. Certain exemplary embodiments described herein use the latter open loop range checking and pre-calibrated correction of detected signal based on measured source intensity as a primary means of reducing variability between readings.

Exemplary light sources, preferably producing monochromatic light, include laser light generation; broad band source filtering using dichroic, selective absorption filters (e.g. colored glass), interference filters; or light emitting diodes. Greater monochromaticism of the illumination source light is believed to be advantageous as it can reduce the amount of autofluorescence in the sample container, liquid sample, and surround device construction materials particularly when the monochromaticism is in the NIR spectrum where generally fewer material are excited into autofluorescence. Autofluorescence is preferably avoided because it tends to raise the background signal and reduce the signal to noise ratio of the system and could reduce the limit of detection and resolution of the system.

The beam angle and coherence of the source light affect the scatter pattern and representation of the sample. An illumination source that spreads to close to the container surface can scatter light directly into the measurement detector by acting as a light pipe to the detector or directly reflecting or refracting light into the measurement detector. To avoid this potential source of background it is preferred to illuminate a core but large section of the sample within the field of view of the sample detector. Typically, the larger the illuminated volume within the field of view of the detector the more representative the result is of the entire sample bulk volume.

Ambient light rejection is of particular concern for an optical device with a low limit of detection or fine resolution near a cutoff value. It is preferable to reduce or remove the background noise levels. It is known in the art of optical design several ways of removing ambient light but these methods apparently have yet to be applied to the specific application of determining sample adequacy prior to analytical testing with a light scattering method. One means of design is to polarize the illumination source light and then detect only light of a similar polarization thereby removing randomly polarized light from other potential ambient sources. This reduces the level of ambient light. If the spectrum of the ambient light is known then filtering those known wavelengths out of the detectable light is another means of rejecting ambient light. Modulating the intensity of the illumination source at a frequency both different and distinguishable from the frequency of intensity variations in common ambient light sources allows an electronic signal rejection or algorithmic post processing signal rejection of ambient light from the detected signal. For example, an analog Butterworth bandpass filter or a discrete ChebyChev filtering could distinguish a 10 Hz illumination source light from a 50-60 Hz light ambient light source and it's harmonics.

The most basic method of ambient light rejection is physically isolating/blocking the sample and detector from ambient light. Isolation in an automated system can increase cost, quality control, assembly complexity, or require additional moving parts and controls. Accordingly, certain embodiments reject light using other means while establishing a more accessible optical pathway.

Detection wavelengths are generally selected based on available detector sensitivity in a wavelength of interest. It is preferred that the detector's responsiveness is acceptable in the range of light that is scattered from the sample. In certain exemplary embodiments, the latter range is the same wavelength as the illumination source light.

Reflectance from the air liquid interface of the meniscus formed by the sample in the sample container may negatively impact signal so placement of the detectable illuminated sample volume away from the meniscus by positioning the detector appropriately can improve the signal to noise ratio and limits volumetric effects on the scattered signal.

The sample container or its openings permits the transmission of both the illuminated and scattered light. The container itself may be beneficially used to filter, polarize, or simply transmit the light of interest. An embodiment of the current disclosure would select a sample container made of material with a high transmittance of the illumination source light in the wavelength of interest. The geometry of the container may be designed to avoid light piping of the illumination source light or ambient light to the measurement detector. The geometry of the container may lens the beam angle of the illumination source and/or detected scatter to reduce or enlarge the core illuminated sample volume visible to the measurement detector to enhance the determination of sample adequacy. Embodiments of the present disclosure use the sample container as a means to control the beam's angle of illumination or detecting light. Additional embodiments use separate optical manipulations with lenses or other optical elements within the illuminating or scattered lights path.

A sample assurance reader/meter may be comprised of a single or a plurality of channels to read one or more samples in unison or separately. The reader may include a homogenization mechanism such as an orbital or linear agitator/shaker that mixes the sample prior to or during a reading. Alternatively the meter may be controlled by a central software or programmable logic system that allows separate orbital or linear agitator/shaker to homogenize the sample before or during readings. The agitator/shaker may be a robotic arm that moves the sample container in a fashion that homogenizes the sample. The agitator/shaker mechanism may also be a pipettor, for example a pipettor or the dispense action of the pipettor used when a sample is transferred to the sample container used to measure the sample assurance.

The reader or the sample container may or may not be rotated/scanned during the reading or during multiple readings that algorithmically combine to report a single determination of the samples assurance level. A benefit of rotating/scanning the sample would be to allow a more representative interpretation of the sample assurance level and/or reduce dependency on the optical clarity (lack of scratches, digs, etc.) of the sample container.

A sample assurance reader may be comprised of a communication architecture that is compatible with a larger automated systems architecture to control the timing and functionality of the reader. The reader may be compromised of a detector board that amplifies the small currents or voltages generated by the detector. One instance of the detector board contains 8 measurement detectors and their amplification circuits. A reader may be comprised of an illumination board that illuminates the sample with source light. On instance of the illumination board contained 8 LED's and their driver circuits. The reader may be comprised of a power distribution architecture that takes externally provided electrical power and distributes it to functional electronics in the module. It is conceived at the time of development that the electronics used to power, detect, transmit, or interpret the power and signals used in the device could be mounted remotely from the actual optical measurement location. It is also conceived that adding design provision to improve the electromagnetic compatibility (EMC) for the device such as faraday cage shielding, adding decoupling capacitance, avoiding ground loops, etc. will improve performance of the device in a wide variety of environments.

In practice all sample containers that are plastic or glass have a level of haze or scratches that can alter the light scattering pattern. Exemplary embodiments utilize rotating/scanning of the sample container to mitigate some of these effects. Other exemplary embodiments employ measurement detectors in a location that is unlikely to be scratched in use and/or production. Alternatively or in addition to these methods, the sample container could be quality checked for scratches either prior to sample transfer in the automated system or earlier in the production process for the sample container itself. Additionally protective films, pouches, or packaging could be used to protect the scratch free nature of a sample container prior to reading.

Similarly it is beneficial to control and measure in production the turbidity of the transport or assay media that the sample will be mixed with in the collection process. Pre-screening the quality of the media will allow for tighter background level control and hence improved signal to noise performance. Additionally, absolute levels of media turbidity could affect the limit of detection of the system.

DEFINITIONS

A sample is a subset of or an entire entity that is being tested to determine characteristics about the entity. For example, a human may provide a blood sample that will be tested for an HIV viral DNA analyte. The person could be found HIV positive and the viral load of there blood assessed. Common sample types that could benefit from methods described in this document are blood, plasma, urine, tissue scrapes, hair samples, gas samples, liquid samples, solid samples, particulate samples depending on the application and industry.

Sample assurance is defined as the confidence in the adequacy of a sample.

Sample adequacy is defined as a sample where a valid result is representative or predictive of the true actual status of the entity being tested e.g., the presence or absence of a specific virus in an individual such as HPV16.

The invention will now be described in more detail with respect to the following, specific, non-limiting examples.

EXAMPLES

Example 1

Sample Adequacy Control Measurement Systems

Referring now to FIG. 1, a Sample Adequacy Control Measurement System ("SAM") 100 capable of measuring the turbidity of a sample is shown. A sample is provided in container 150 which is supported by housing 120. Light source 102 which comprises an LED emits light that travels along a schematically shown illumination beam path 104 and illuminates sample 112. Light is reflected or scattered from particles suspended within sample 112 and travels along emitted beam path 106 to sample detector 108. Sample 112 has sufficient volume that meniscus 113 is above the portion of sample 112 that reflects or scatters light, some of which travels along emitted beam path 106. Reference detector 110 detects light transmitted from light source 102 along reference beam path 111 to allow correction for the intensity of light emitted from light source 102. The intensity of light detected by reference detector 110 may be used to calibrate the light output from light source 102 (e.g., by varying the voltage to this light source), as a reference such that turbidity can be calculated from comparison of the light signal detected by sample detector 108 and reference detector 110, and as an indicator of whether light source 102 is functioning properly or is malfunctioning and should be replaced.

The reference detector can be used to monitor the variations in LED light output. Standard commercially available or custom turbidity calibrators (solutions of characterized particle/cell suspensions in differing particle/cell densities or sizes) can be used to map a relationship between the measurement detector and the level of turbidity. Additionally, mapping a relationship of turbidity as a function of the measurement detector and the reference detector can allow for correction of turbidity readings with reasonable variations of the light source. One exemplary mapping would be a linear mapping near the cutoff range where the ratio of the measurement detector signal to the reference detector signal maps piecewise linearly to a multiple (e.g. 2 points, 3 points, n-points) point calibration curve.

To avoid the need for many calibration points to handle natural non-linearities in the system the ability to detect if the illumination source is working and detector are working is incorporated. For example, the device may have the illumination source flash at a known frequency to confirm that both detectors and the source are working with or without a sample container present. Confirmation of the optical channel then allows saturated signals to be considered adequate samples in a qualitative determination of sample adequacy. For example, the sample adequacy may be reported simply as positive or alternatively as >200,000 cells/ml for a saturated measurement detector signal. This optical channel self test allows the design to achieve higher resolution by setting the analog to digital converter (ADC) to a finer resolution. Typically, the amplified signal may vary from 0-12V from the detector. If a 16 bit ADC is set to 0.7V to cover the range of approximately 0-49 NTU the resolution near the cutoff can improve and reduce the possibility of a grey zone in the sample assurance determination. Alternatively, the full dynamic range needed to report a unique quantitative result on the whole population of women may require detection near 700 FNU. This would require the ADC to be set at 10V range and thereby could significantly reduce the resolution of the reader near the cutoff. When a quantitative measurement of sample adequacy is desired, the gain may be actively changed within the reading or through additional readings of the turbidity to achieve better sensitivity through the range of turbidity. This device can also allows for a binary determination of sample adequacy so active gain control is not required.

The reader can report corrected readings to the automated system via a communications port. The software can then compare the value to a predefined absolute cutoff value for that sample type. Samples with a light scatter reading greater than or equal to the cutoff can be considered adequate. Samples with a value less than the cutoff can be considered inadequate in cellularity.

Figure 2:
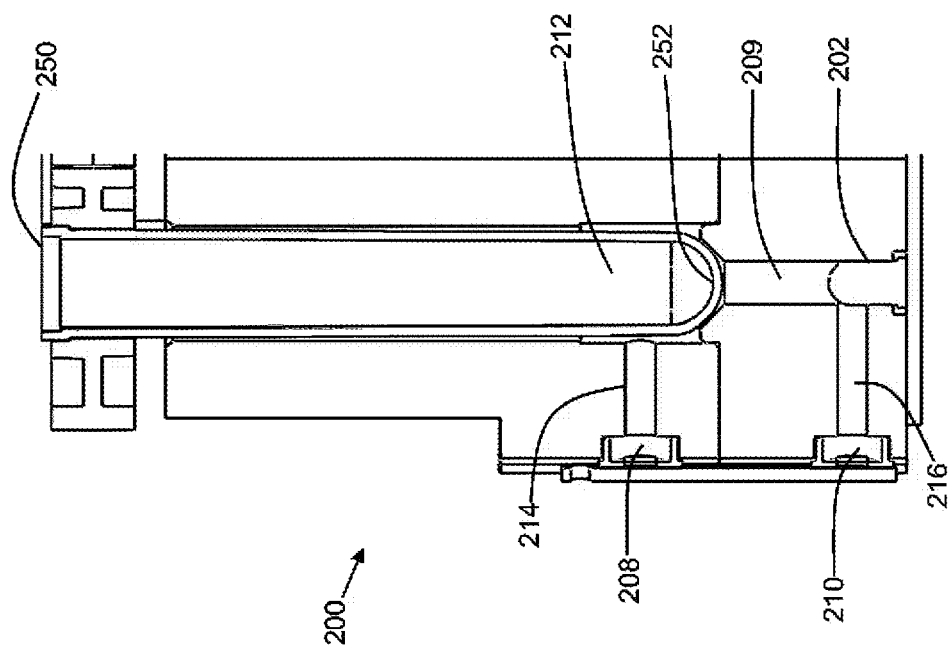
FIG. 2 generally comprises a SAM.

Referring now to FIG. 2, a Sample Adequacy Control Measurement System ("SAM") 200 capable of measuring the turbidity of a sample is shown. In this embodiment, emitted and detected light travels through beam channels which can reduce background arising from ambient light, and from light scattered from defects in sample container 150. Light emitted from light source 202 travels through input beam channel 209 and illuminates sample 212. Particles suspended within sample 212 reflect or scatter light, some of which travels through emitted beam channel 214 to sample detector 208. Light scattered from scratches or imperfections in the illuminated portion 252 of sample container 250 is prevented from traveling to detector 208 by emitted beam channel 214, potentially decreasing background and making turbidity measurements relatively less sensitive to scratches in the illuminated portion 252 of sample container 250. Similarly, reference detector 210 detects light transmitted from light source 202 along reference beam channel 216, which excludes reflected, scattered, and ambient light, and accordingly can decrease the background signal reaching reference detector 210 and improving the reliability of this measurement.

Example 2

Extraction Tube Unit

Figure 3:
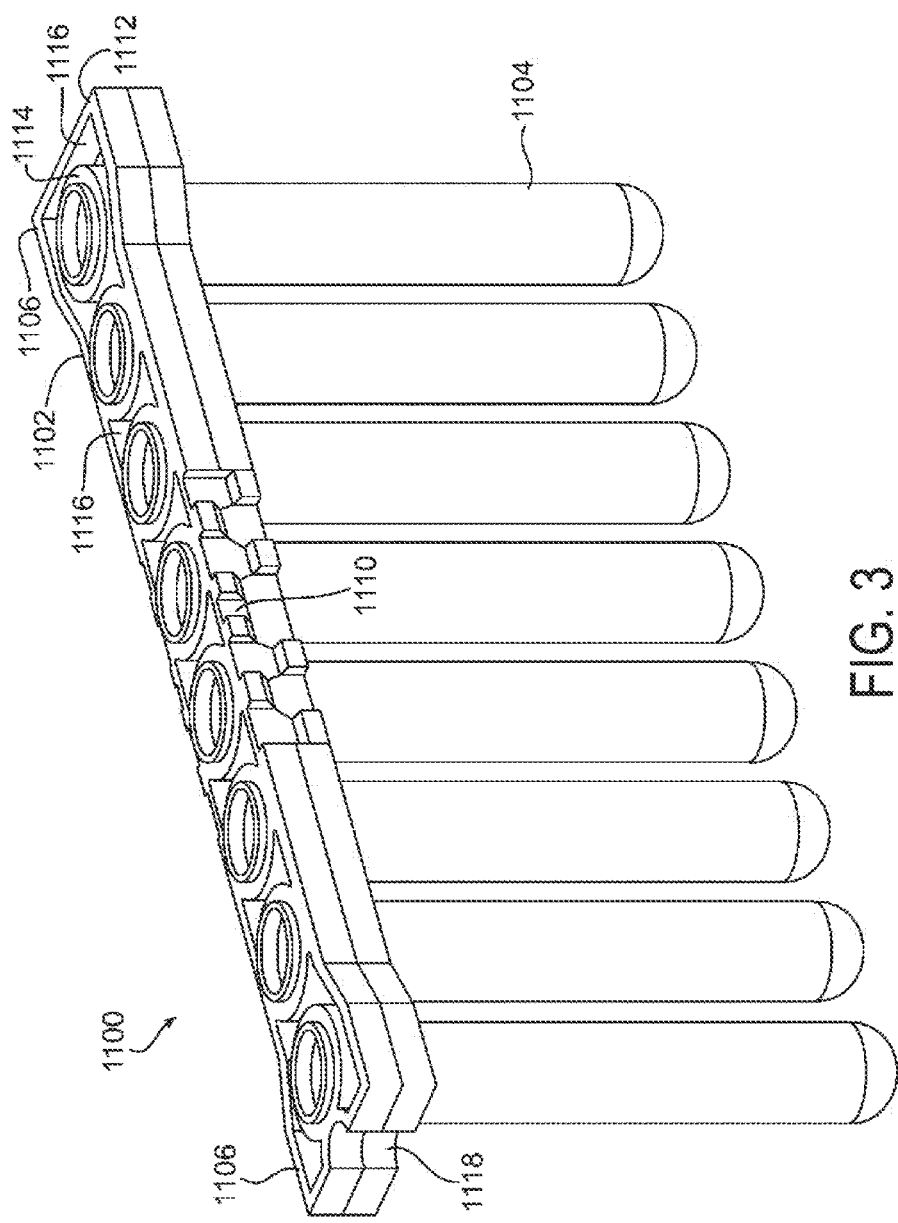
FIG. 3 generally comprises a multi-well sample container referred to as an Extraction Tube Unit ("ETU").

FIG. 3 illustrates an exemplary embodiment of an extraction tube unit ("ETU") 1100 that may be used as an intermediary vessel in the processes and systems described herein or in other systems. This ETU 1100 may be similar or identical to the one described with respect to FIGS. 4-6. Typically an ETU will include an identifying feature, such as a barcode, and a gripping surface that facilitates holding and/or movement of the ETU by an automated system. An individual sample position or test tube within an ETU may be referred to as an ETU tube or ETU position.

The exemplary ETU 1100 comprises a frame 1102 and a number of test tubes 1104. In this embodiment, eight test tubes 1104 are provided, and each ETU corresponds to a column of a typical 96-well sample plate. However, twelve-tube ETUs and ETUs having other numbers of test tubes may be used in other embodiments. The frame 1102 may comprises a rigid structure that has suitable strength to convey the tubes 1104 and samples contained therein throughout the processing steps without substantially deforming under applied loads. The material also should be stable and sufficiently strong at the operating temperatures within the system. Suitable materials may include, for example, metal, wood, or plastic (e.g., nylon, polyvinylchloride, polypropylene, polystyrenes such as ABS and HIPS, etc.).

The tubes 1104 may comprise any suitable shape. The embodiment depicted has a round bottom which facilitates vortex mixing and minimizes pipetting dead volume. Conical bottom tubes would also share these characteristics. Other shapes, such as flat-bottomed shapes, may be used in other embodiments. The tubes 1104 may be configured to facilitate upstream or downstream processing. For example, the distance between each tube 1104 may be about 18 mm, which corresponds to about twice the space between the wells in a standard 96-well microplate. This spacing permits a fixed-width 4-channel pipettor to draw samples from 4 tubes within the ETU and dispense the samples into alternating positions in a 96-well microplate, which facilitates transfer of samples. The tubes 1104 may be made of any suitable material, such as glass or plastic. To facilitate optical testing, such as in a turbidity test, the test tubes 1104 preferably is formed in part or entirely from a transparent or semi-transparent material having sufficient clarity and transparency to permit the desired testing. The test tubes 1104 may be formed integrally with the frame 1102 (such as by forming them from the same material that forms the frame 1102 or molding them in place within the frame 1102), or formed separately and joined to the frame (such as by press-fitment, adhesives, fasteners, threads formed on the test tubes 1104, and so on).

The test tubes 1104 are arranged in a line along the length of the frame 1102, but in other embodiments, in which the frame 1102 may have different shapes, the test tubes 1104 may be arranged in any other suitable array or pattern.

Figure 11:
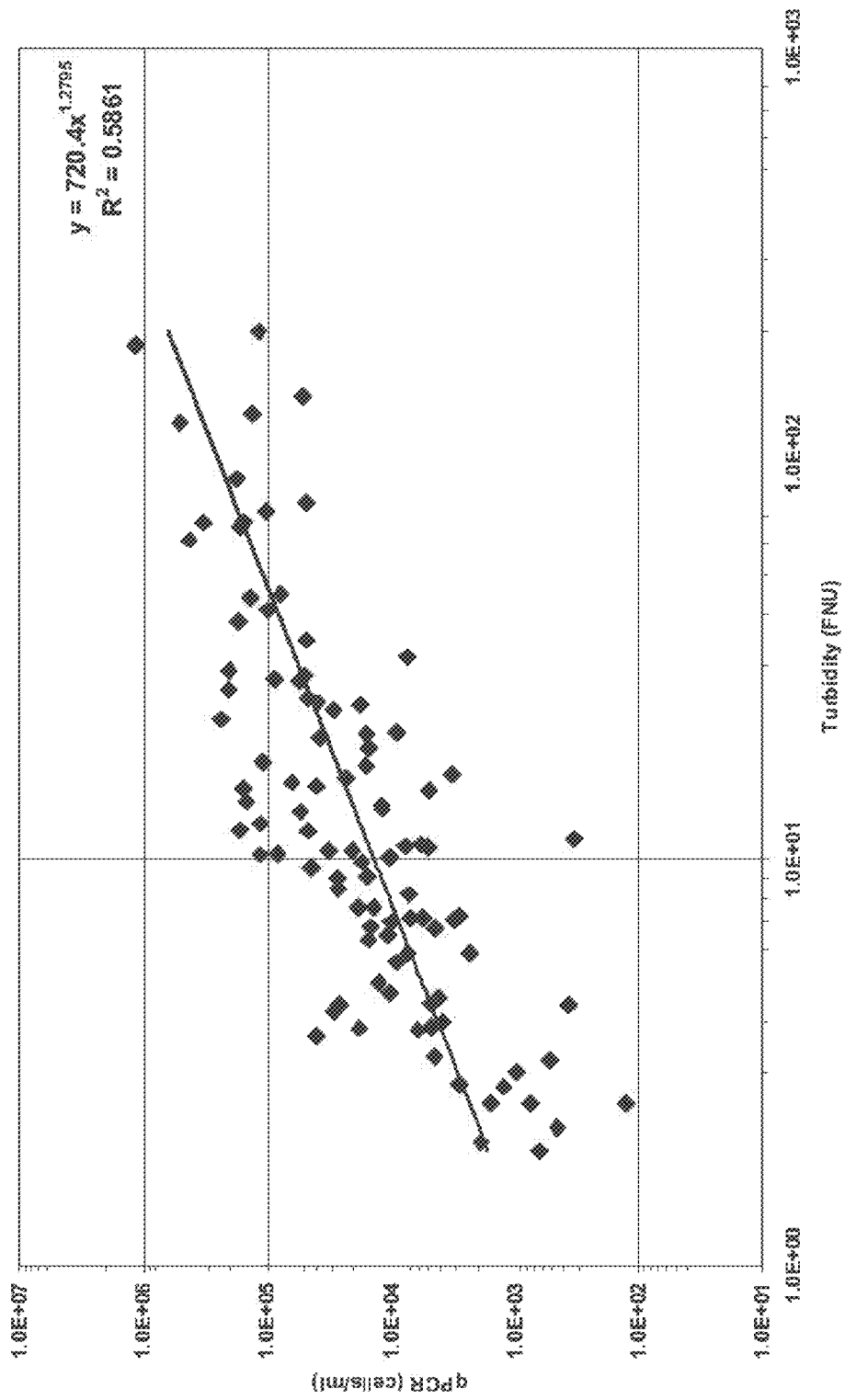
FIG. 11 shows comparision of cellularity determined by qPCR and turbidity values.

As shown in FIG. 11, frame 1102 is elongated, and may have enlarged ends 1106 that result in recesses being formed along one or both long sides of the frame 1102. In the shown embodiment, the frame has a "dog bone" shape as viewed from above. As a result of providing the enlarged ends 1106, the recesses create spaces between adjacent ETUs when multiple ETUs are tightly packed together. This permits a gripper 1200, described below, to access and individually grasp each ETU 1100.

The frame may have a horizontal groove 1108 and a vertical groove 1110 on each long side. The grooves 1108, 1110 may be formed using any suitable manufacturing process. In the shown embodiment, the ETU frame 1102 is molded from plastic in a 2-part mold. An upper mold half forms the top of the frame 1102, and a lower mold part forms the bottom of the frame 1102. This arrangement has been found to be favorable in at least some embodiments because it permits the frame 1102 to be easily and inexpensively formed with a rigid outer perimeter wall 1112, cylindrical bosses 1114 to support each tube 1104, and one or more cutouts or recesses 1116 between the perimeter wall 1112 and bosses 1114. This produces a frame 1102 that is rigid, but lightweight and consumes less plastic or other fabrication materials. While the vertical grooves 1110 are readily formed using a simple 2-part molding process, it may be necessary to use an side insert form the horizontal grooves 1108. The need for such additional molding steps and expense has been eliminated in the embodiment of FIG. 11 by forming the horizontal groove 1108 in staggered segments. In this embodiment, upper faces formed on the bottom half of the mold form the downward-facing portions (i.e., the upper edge) of the horizontal groove 1108, and downward faces of the upper mold half form the upward facing portions (i.e., the lower edge) of the horizontal groove 1108. Of course, any other suitable manufacturing method may be used in other embodiments.

Example 3

Multi-Channel Sample Adequacy Control Measurement Systems

This example describes exemplary embodiments of a Sample Adequacy Control Measurement System ("SAM") adapted for use with a multi-channel sample container such as an Extraction Tube Unit ("ETU"). The ETU may be similar or identical to those described in Example 2.

Figure 4:
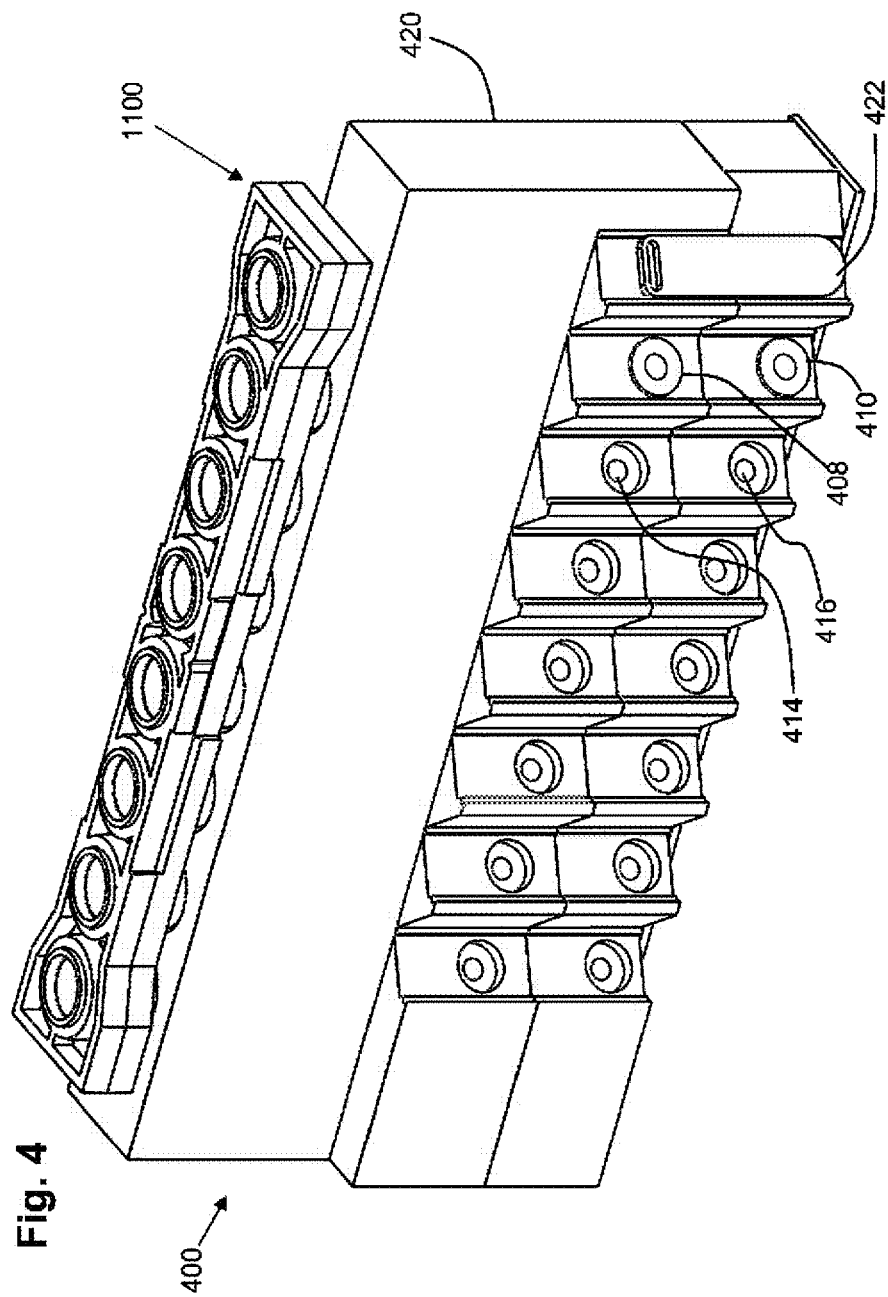
FIG. 4 generally comprises an 8-channel SAM that may be used with samples contained in an ETU.

Referring now to FIG. 4, SAM 400 includes housing 420 that supports ETU 1100. Light sources, detectors, and tubes of the ETU are individually configured similarly to the configurations described in Example 1. In the depicted embodiment each ETU has its own light source, sample detector, and reference detector, though not all are shown or labeled in the figure. Light emitted from a light source beneath each sample illuminates each sample. Particles suspended within each sample reflect or scatter light, some of which travels through each emitted beam channel 414 to each sample detector 408. Each reference detector 410 detects light transmitted from each light source along each reference beam channel 416. Each sample detector and reference detector is mounted to a support 422 which may comprise a printed circuit board.

The illumination source is either a red or a NIR LED with a five degree or tighter beam angle that is illuminating a PS, PETG, PP, PC, PMMA, glass, or other transparent material sample container (5 mL round bottom test tube shown below with a 1.5 mL of sample media liquid level). The beam angle is sufficiently narrow to avoid illuminating the walls of the tube before the meniscus is reached. Additionally, the beam is directed at a curvature of the tube that is parallel to the incident beam such that the sample container wall is unlikely to act as a light pipe (avoids total internal reflection and partial internal reflections). The illumination beam has a small spot size when entering the tube which reduces the size of a scratch free surface needed for illumination. The measurement detectors field of view includes a majority of the illuminated core and little of the unilluminated core to reject ambient light and secondary scattering from reflections rather than primary illumination.

In the embodiment depicted in FIG. 4, each detector is situated to detect light emitted along a beam path at an angle offset from the long axis of the ETU. In this configuration the emitted beam path travels through a protected surface of the ETU, i.e., portion of the ETU that is less likely to rub against another surface during use and accordingly is protected from scratches. The surfaces most likely to be scratched on the tube are on the exterior planes that are tangent to all the tubes outer diameters. However, for the rightmost tube of the ETU in the depicted configuration, the emitted beam path travels through a potentially exposed location. This difference in the rightmost tube is avoided in the embodiment depicted in FIG. 5. A less scratch tolerant embodiment is also envisioned and would use a single detector board with all 8 measurement detectors.

Figure 5:
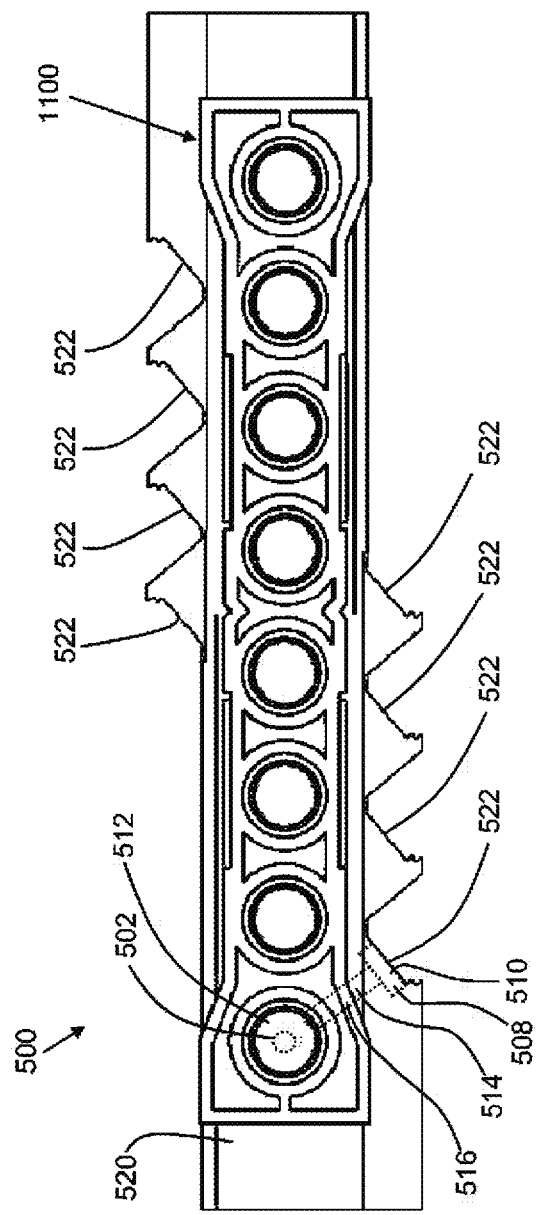
FIG. 5 generally comprises an 8-channel SAM that may be used with samples contained in an ETU.

Referring now to FIG. 5, SAM 500 is depicted in an overhead view. The emitted beam path travels through a protected surface for each of the tubes in ETU 1100. In this embodiment, the detector for the four leftmost tubes are situated on a different side of the ETU than the four rightmost tube. In the depicted embodiment each ETU has its own light source, sample detector, and reference detector, though not all are shown or labeled in the figure. Each sample detector and reference detector is mounted to a support 522 which may comprise a printed circuit board. Light emitted from light source 502 travels through an input beam channel and illuminates sample 512. Particles suspended within sample 512 reflect or scatter light, some of which travels through emitted beam channel 514 to sample detector 508. Reference detector 510 detects light transmitted from light source 502 along reference beam channel 516.

A sample contained in each individual tube of ETU 1100 is illuminated from beneath by a light source, and a portion of the light scattered or reflected from particles contained within each sample light travels down light path 414 detected by sample detector 408.

Figure 6:
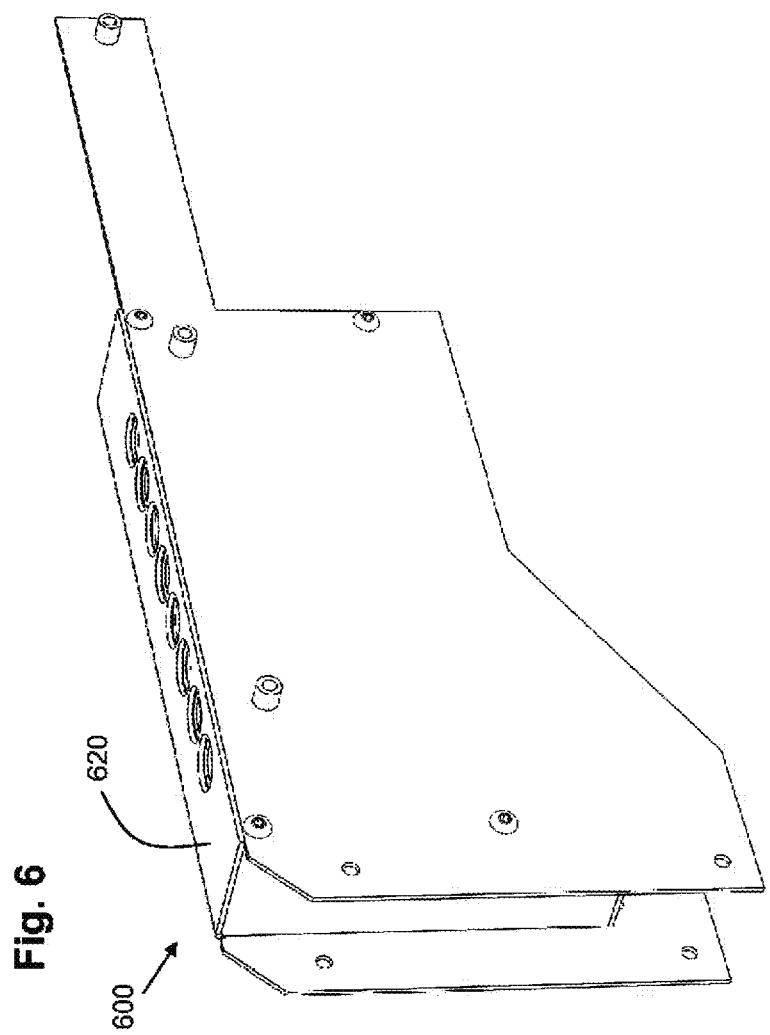
FIG. 6 generally comprises a modular 8-channel SAM which may be incorporated as a module within a sample processing system.

Referring now to FIG. 6, an 8-channel SAM 600 is depicted which may be incorporated as a module within a sample processing system. Housing 620 contains the components of a multi-channel SAM similar to those described above which may be mounted within an automated system. For example, an automated system may use individual containers or ETUs or similar containers as an intermediary vessel in the processes and systems. Example of such systems are described in U.S. application Ser. No. 12/062,950, entitled "SAMPLE PREPARATION SYSTEM AND METHOD FOR PROCESSING CERVICAL SPECIMENS," filed Apr. 4, 2008, U.S. application Ser. No. 12/588,304, entitled "AUTOMATED ASSAY AND SYSTEM," filed Oct. 9, 2009, and in U.S. application Ser. No. 12/588,306, entitled "Open Platform Automated Sample Processing System," filed Oct. 9, 2009, each of which is hereby incorporated by reference in its entirety.

Figure 27:
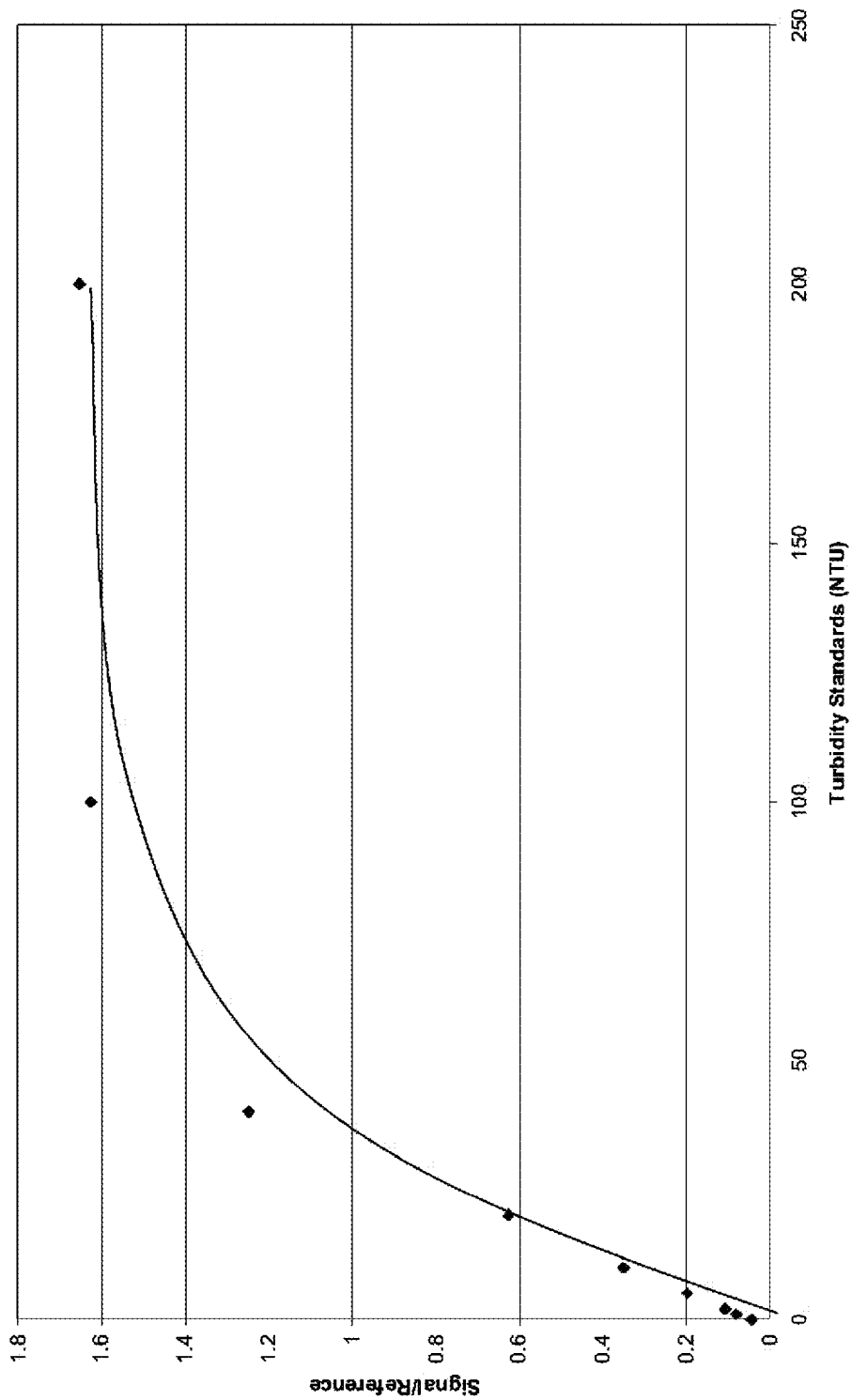
FIG. 27 shows the signal/reference measurements of turbidity standards for a working model of a Sample Adequacy Control Measurement System ("SAM").

FIG. 27 shows the signal/reference measurements of turbidity standards for a working model of a Sample Adequacy Control Measurement System ("SAM").

Figure 28:
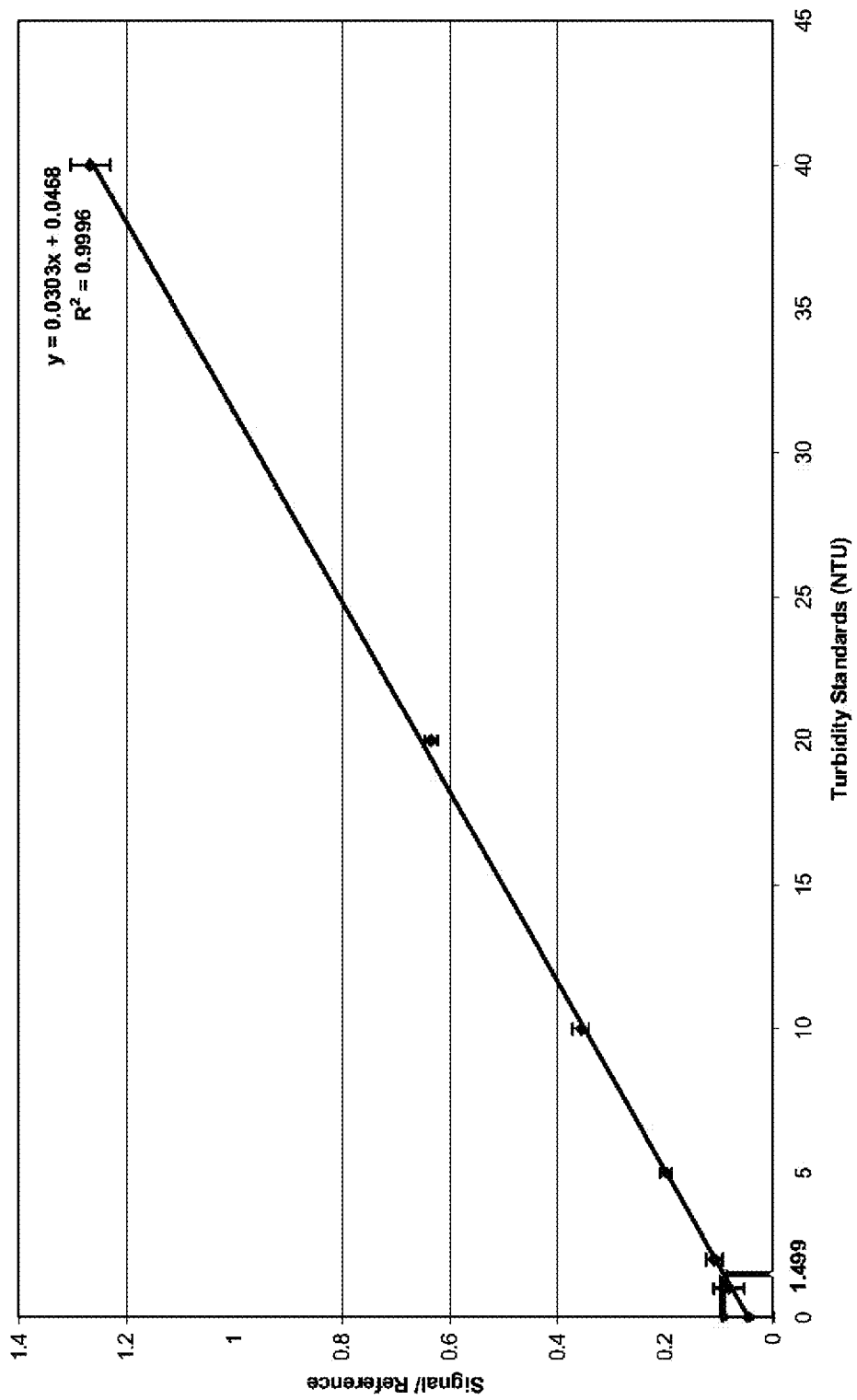
FIG. 28 shows a calibration curve for a working model of an 8-channel SAM.

FIG. 28 shows a calibration curve for a working model of an 8-channel SAM.

Figure 29:
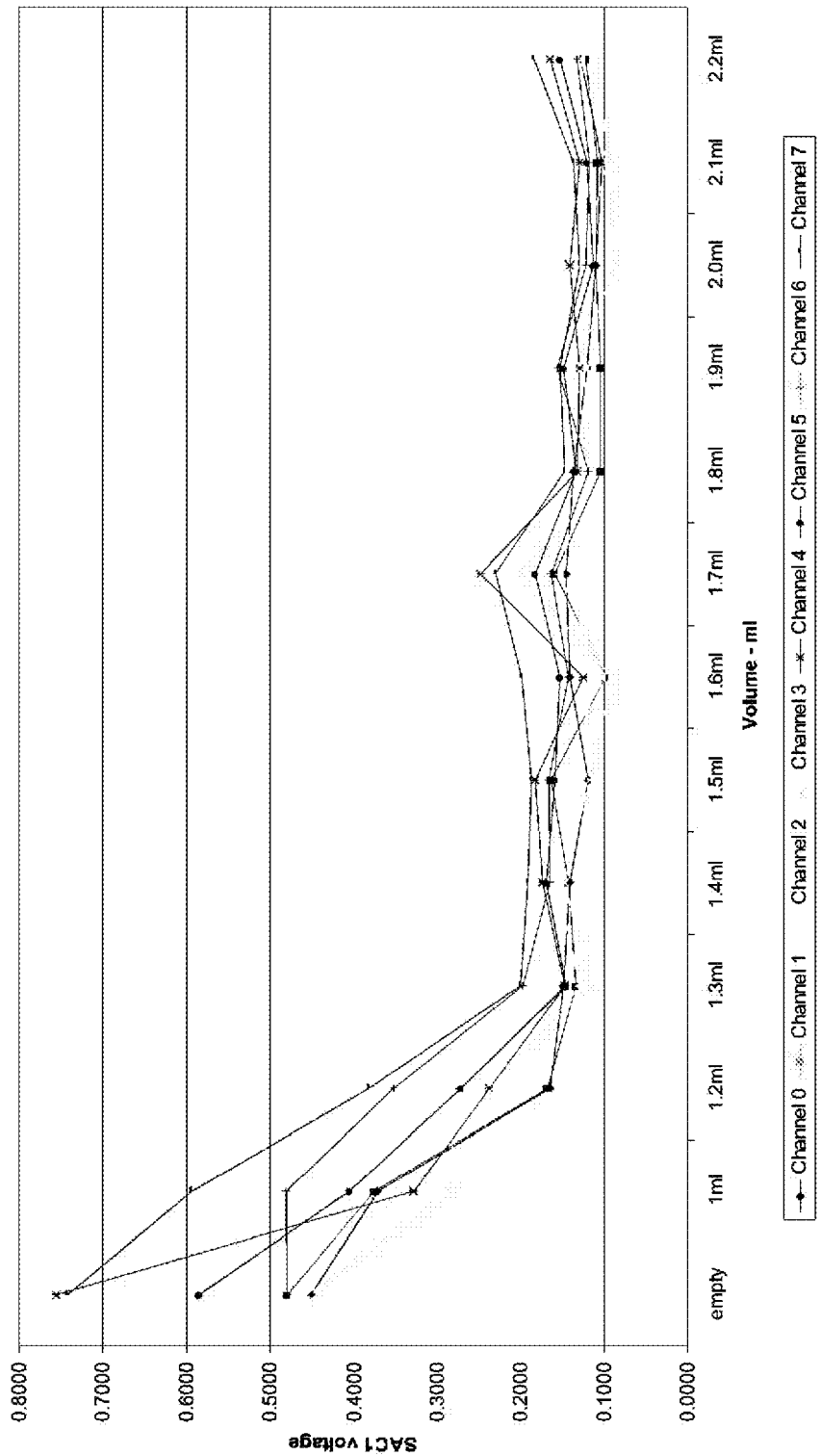
FIG. 29 shows the dependency on sample volume in each channel of a working model of an 8-channel SAM.

FIG. 29 shows the dependency on sample volume in each channel of a working model of an 8-channel SAM.

Figure 30:
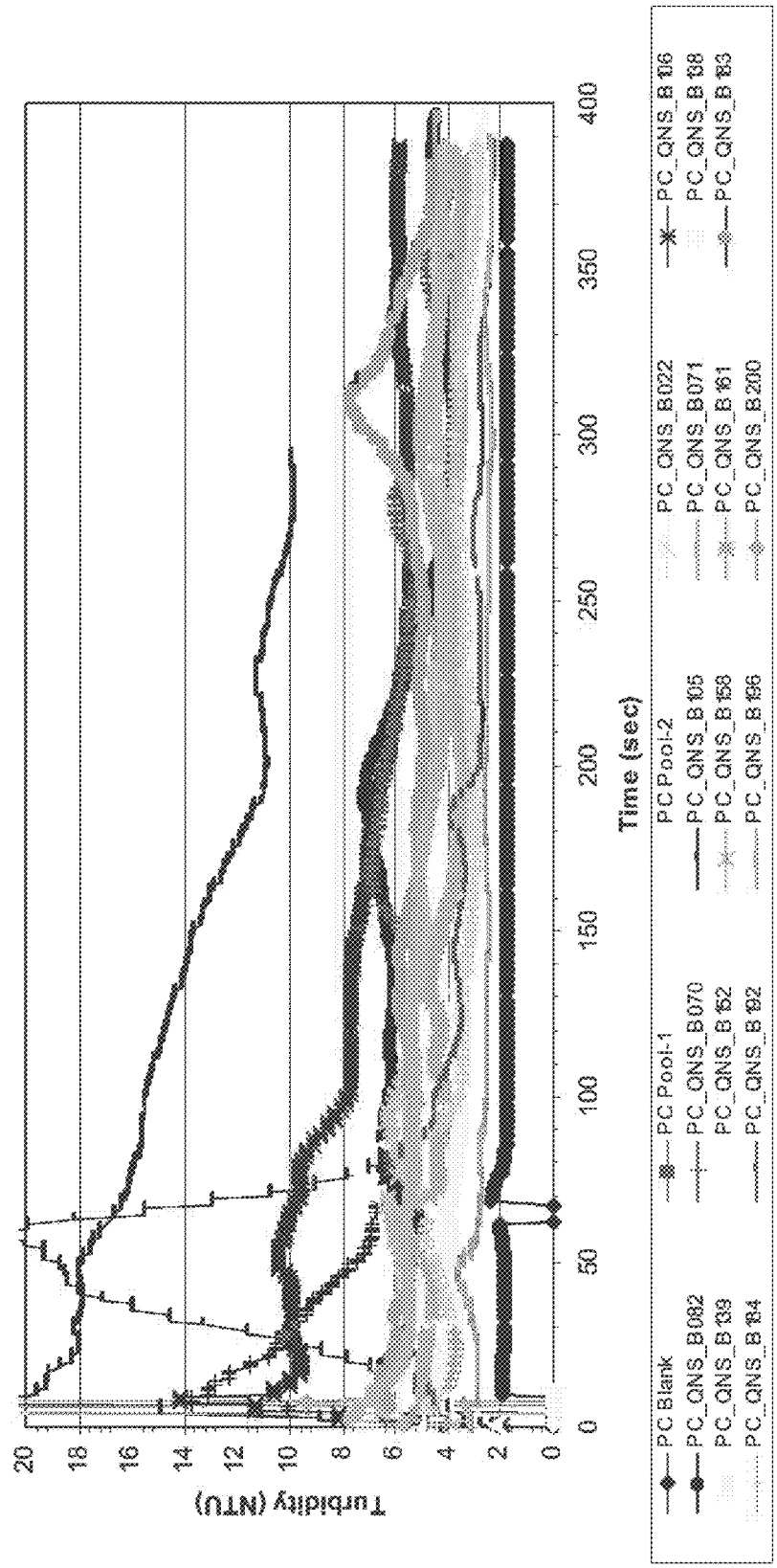
FIG. 30 shows the settling of samples over time and consequences for turbidity measurement.

FIG. 30 shows the settling of samples over time and consequences for turbidity measurement.

Example 4

Comparison of 8-Channel Detection System with Hach Turbidimeter

Figure 31:
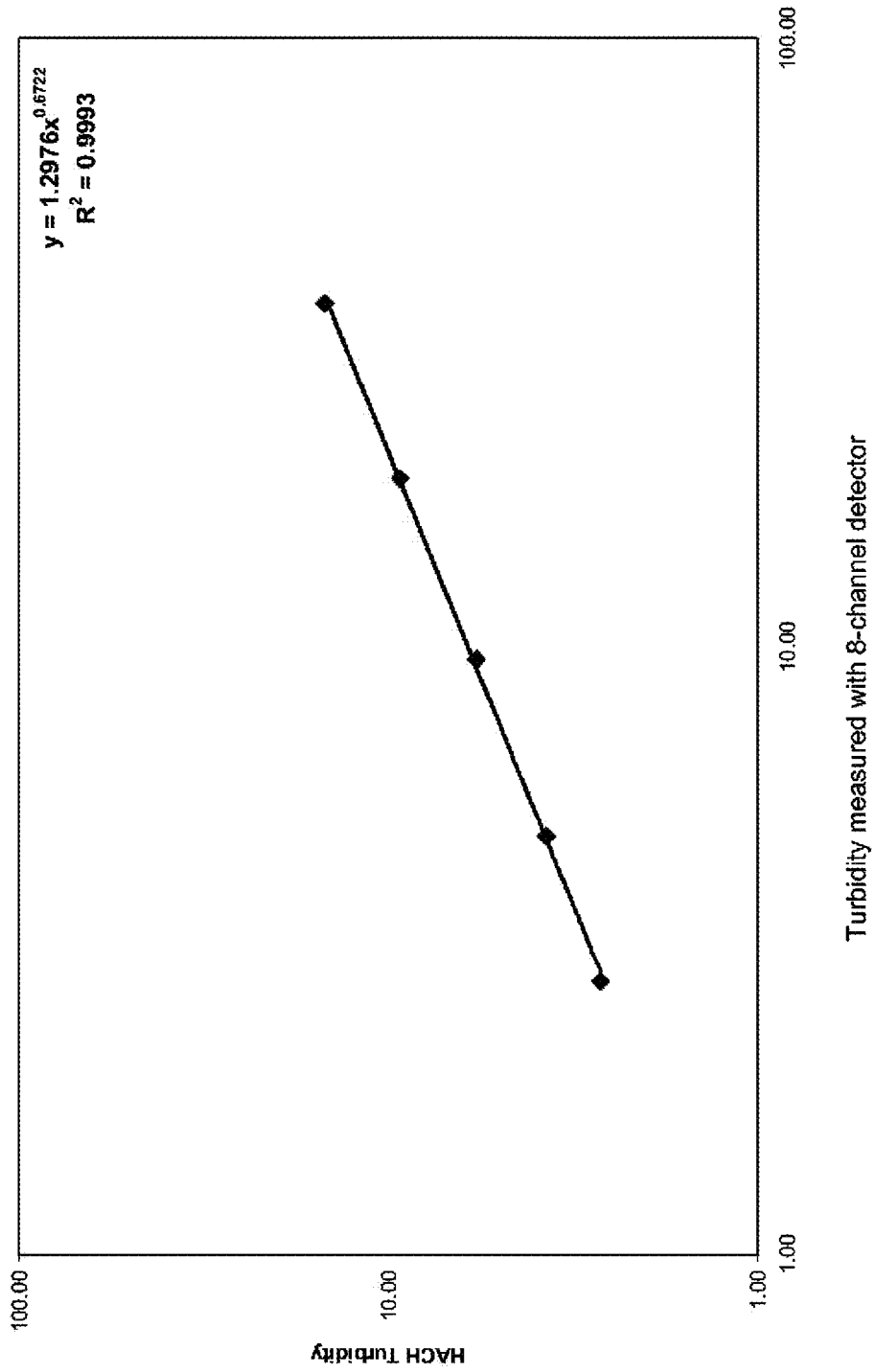
FIG. 31 shows that turbidity measurements by an 8-channel SAM correlated with turbidity measured by a Hach Meter for five turbidity standards ($R^2=0.9993$).
Figure 32:
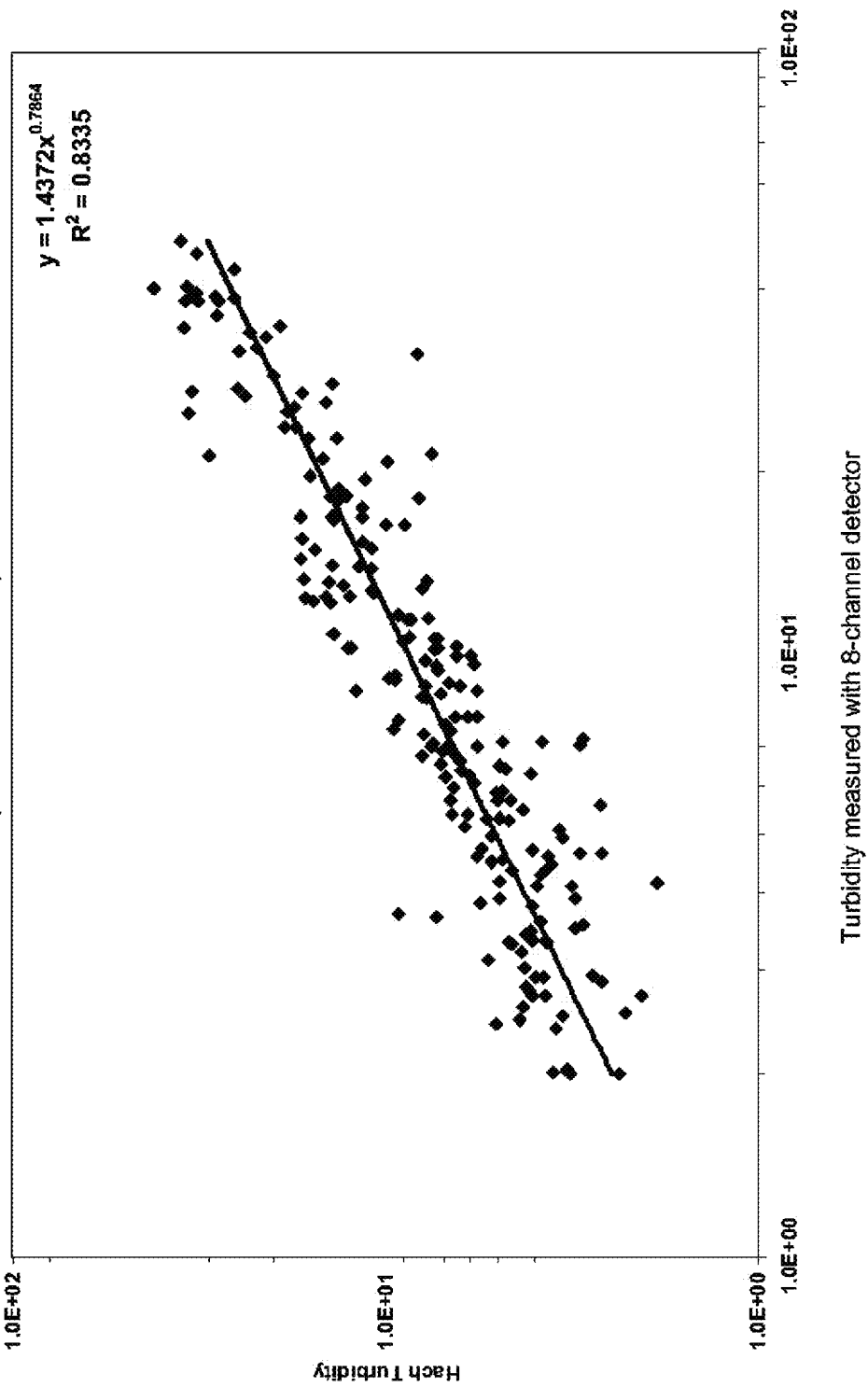
FIG. 32 shows that turbidity measurements by an 8-channel SAM correlated with turbidity measured by a Hach Meter for clinical samples (n=235; $R^2=0.83$).

Turbidity measurements taken using an 8-channel detection system similar to the systems described in Example 3 were compared to turbidity measurements taken using a Hach turbidimeter. Five turbidity standards were measured with each, giving a correlation coefficient $R^2=0.9993$ (FIG. 31). Moreover, referring now to FIG. 32, there was a strong correlation between measurements taken with the Hach meter and 8-channel detection system for clinical specimens in PreservCyt media (n=235; $R^2=0.83$). These results further confirm the validity of measurements obtained with the 8-channel detector system.

Example 5

Turbidity Measurements of Blank Samples

Turbidity of "blank" samples (containing only water or PreservCyt media) was measured. Referring now to FIG. 33, there was very little contribution by blank media to turbidity values. Specifically, 75% of the tubes had readings of 0.2 NTU and below, while 97.5% had readings of 0.9 NTU. These higher readings (>1.0) were apparently due to scratches on the tubes and how they packaged. The effects of scratches can be reduced by taking measures to minimize scratches to tubes during manufacture, packaging, or handling, and/or taking measures to minimize the effect of scratches, such as by transmitting light to the sample and to the detector through portions of the tubes that are less likely to be scratched, for example as described above.

Example 6

Comparison of Sample Cellularity Determined by Turbidity Measurement, Cell Counts, and DNA Quantification This examples describes studies comparing sample cellularity determined by turbidity measurement, direct cell counting by hemacytometry, and DNA quantification by qPCR. The latter two methods, direct cell counting by hemacytometry, and DNA quantification by qPCR, are widely accepted methods of determining cellularity, with direct cell counting by hemacytometry generally considered to be the most accurate method. These experiments were conducted using cervical samples collected from an unbiased population of women in Laurel, Md. Hundreds of samples were collected and evaluated to gather this preliminary data. Certain of these studies used fewer than the total number of patient samples available. PreservCyt (PC) samples were obtained from cervical centers in Laurel, Md. A comparison study was conducted between turbidity measurement, cell counts, and cell density from DNA quantification. A turbidity meter (Laboratory Turbidimeter Model 2100N, Hach Company, Loveland, Co., ("Hach meter")) measured turbidity in 75 mL polystyrene tubes with 2 µL sample aliquots.

Figure 7:
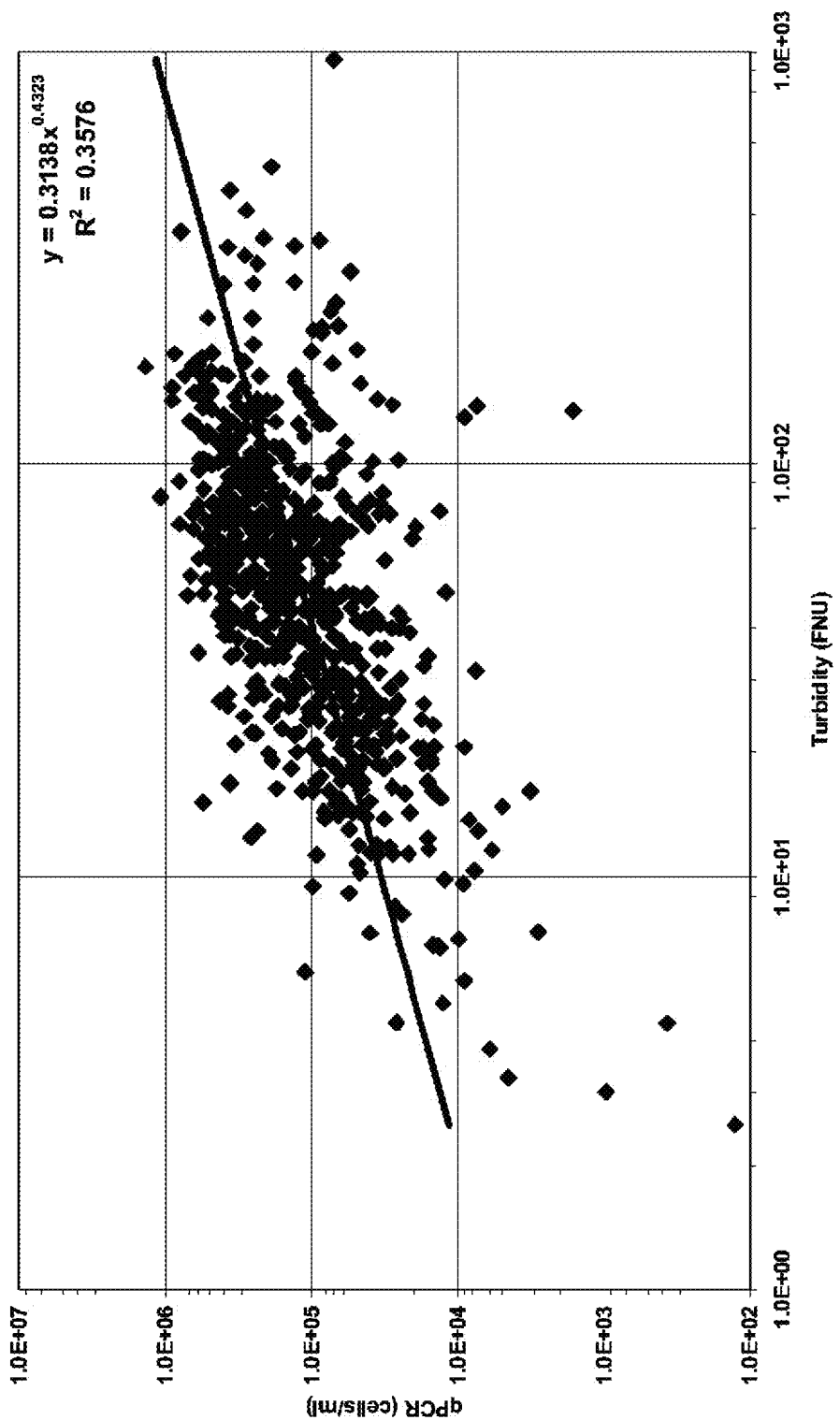
FIGS. 7 and 8 show comparison sample turbidity levels and cellularity determined by qPCR.
Figure 8:
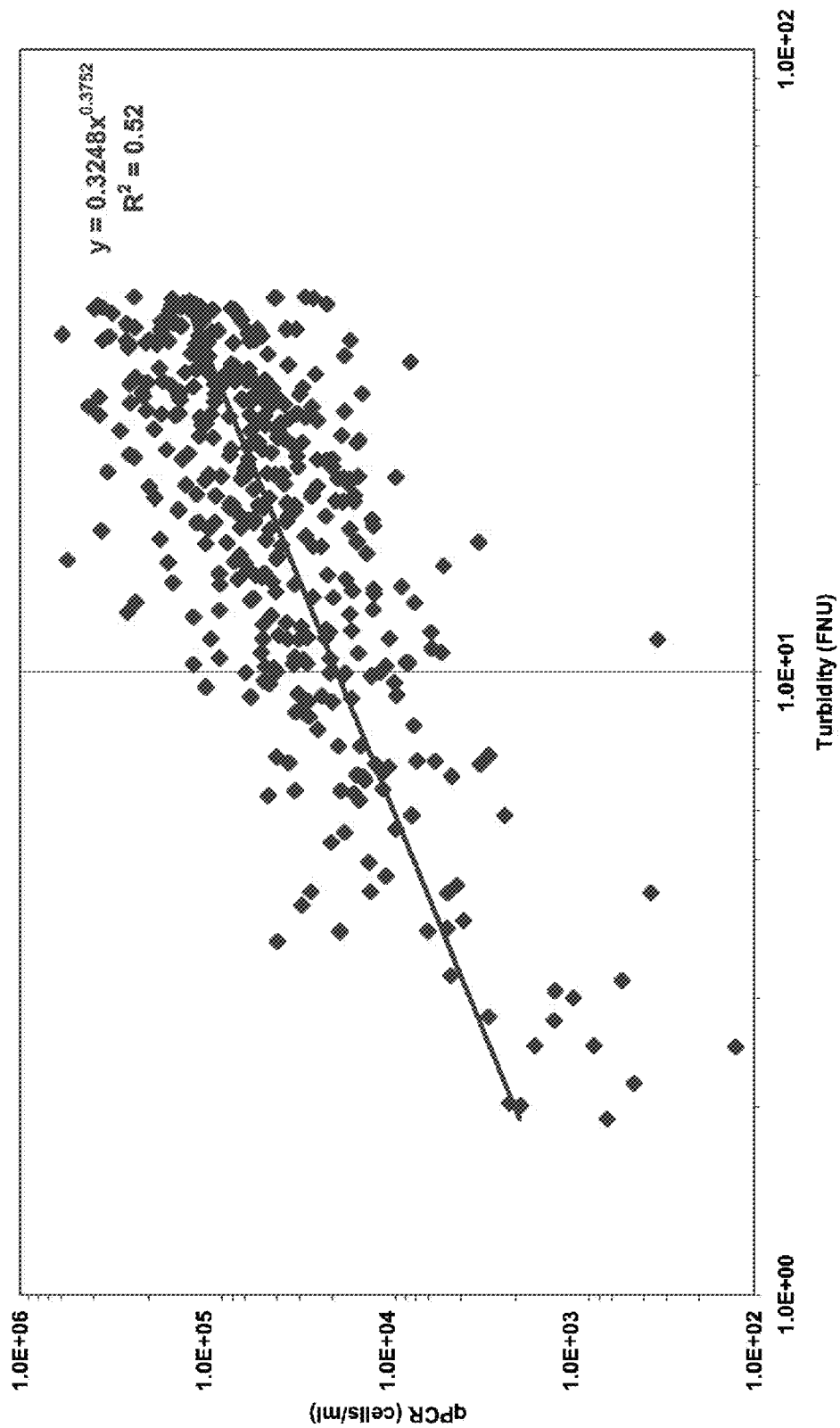

A hemocytometer was used to quantify cells in a 22 µL sample volume (N=99). A Stratagene real-time thermocycler with fluorescence detection was used to quantify DNA using a qPCR ABI Beta Globin control (N=691, N=398). The DNA quantification was then converted to cell density (cells/mL) for comparison. The majority of samples contained 10,000-1,000,000 cells/mL yielding values greater than 10 NTU (FNU). Blank PC Media (N=100) confirmed a 99.5% CI threshold of 2 NTU using the Hach Meter. A logarithmic curve fit through these data is shown in FIG. 7. The Laurel, Md. population displays a medium correlation between qPCR values and turbidity values, with an $R^2$ equal to approx. 0.36. These results illustrate both the nature of the population under test and the actual relationship of turbidity and cellularity near the cutoff for sample adequacy. Oversampling the typical population to find values in the cutoff range (>40 NTU), we found a moderate correlation of $r2=0.52$ (N=398) between turbidity and cell density as measured by Beta Globin (FIG. 8).

Figure 9:
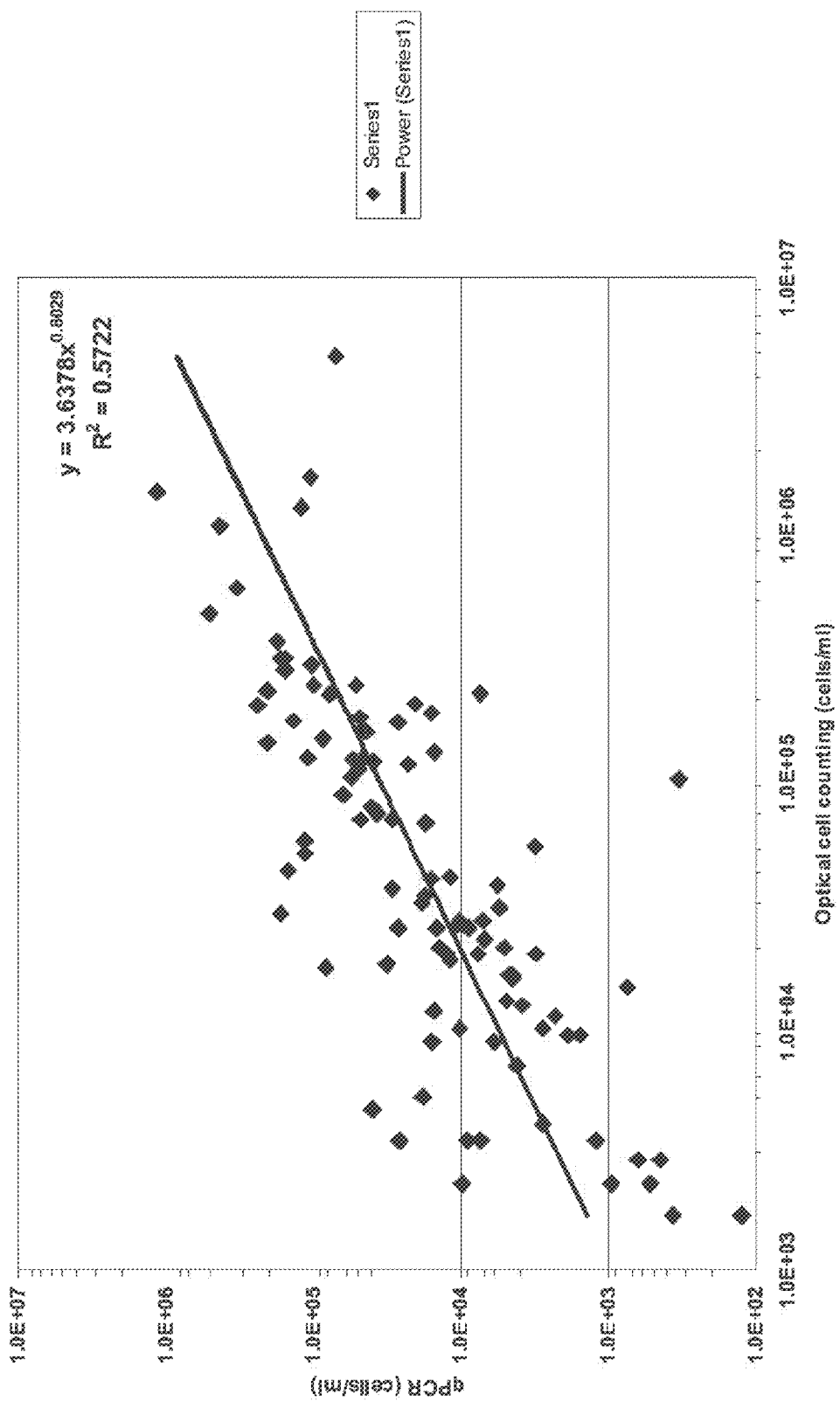
FIG. 9 shows comparision of cellularity determined by optical cell counting and cellularity determined by qPCR.
Figure 10:
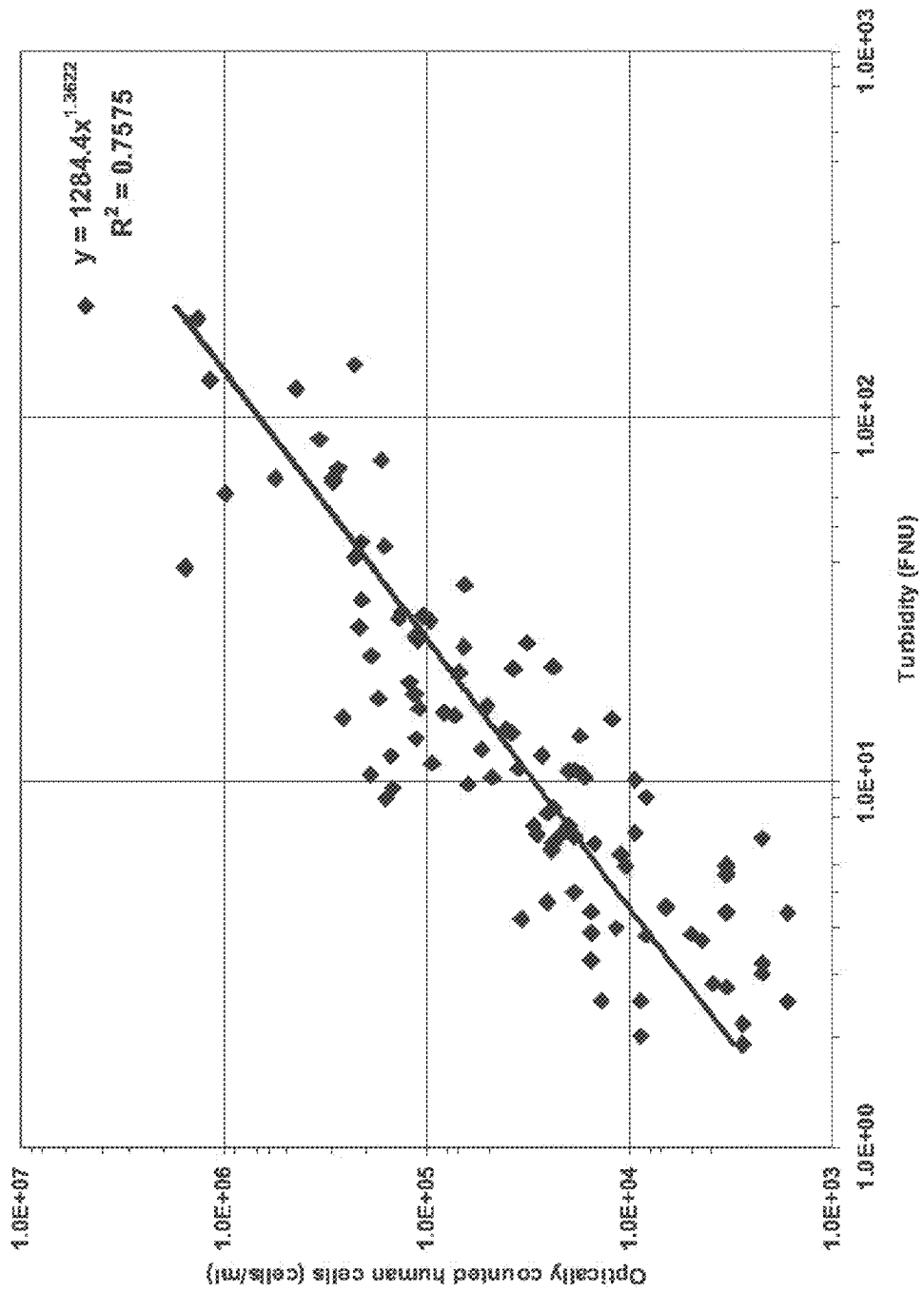
FIG. 10 shows comparision of turbidity levels and cellularity determined by qPCR.

To determine if variability was caused by a specific sample adequacy method or variability in the actual sample both turbidity and qPCR methods were compared to hemocytometry (manual cell counting) estimate of human cells. Comparing with both methods against the gold standard of human cell count we find that both methods have large correlations to cell count but that the turbidity method has a larger correlation. Referring now to FIGS. 9, 10, and 11, the 99 randomly selected low cellularity samples were analyzed for turbidity, Beta Globin qPCR, and hemocytology. The correlation between turbidity measurements and hemocytology ($R^2=0.7586$) was better than the correlation between Beta Globin qPCR and hemocytology ($R^2=0.5722$), (correlation between turbidity and qPCR was $R^2=0.5861$) indicating that turbidity may be a more accurate way to measure cellularity than qPCR.

Figure 12:
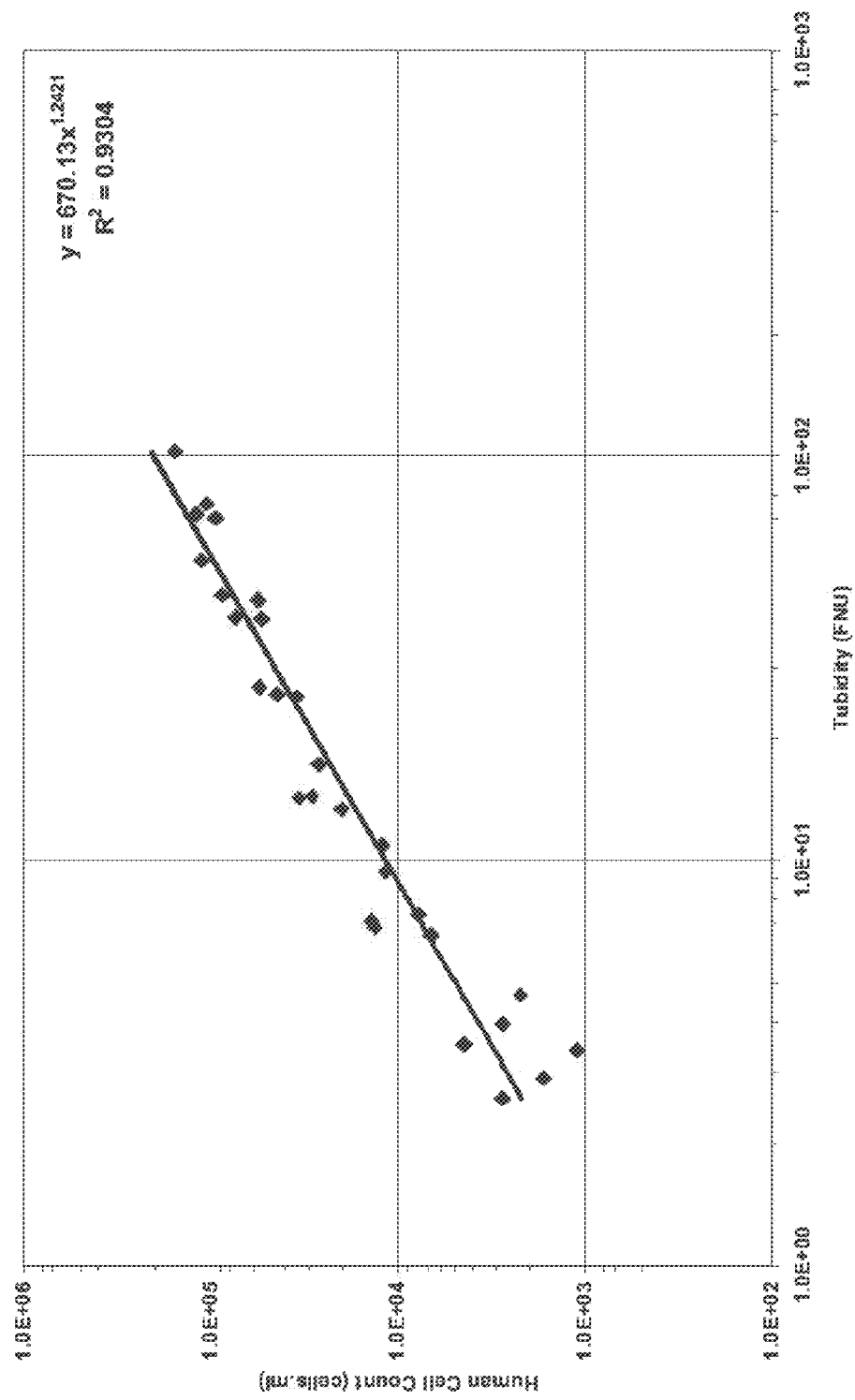
FIG. 12-14 shows comparison of cellularity and turbidity for samples containing bacterial cells, human cells, and mixed bacterial and human cells.
Figure 13:
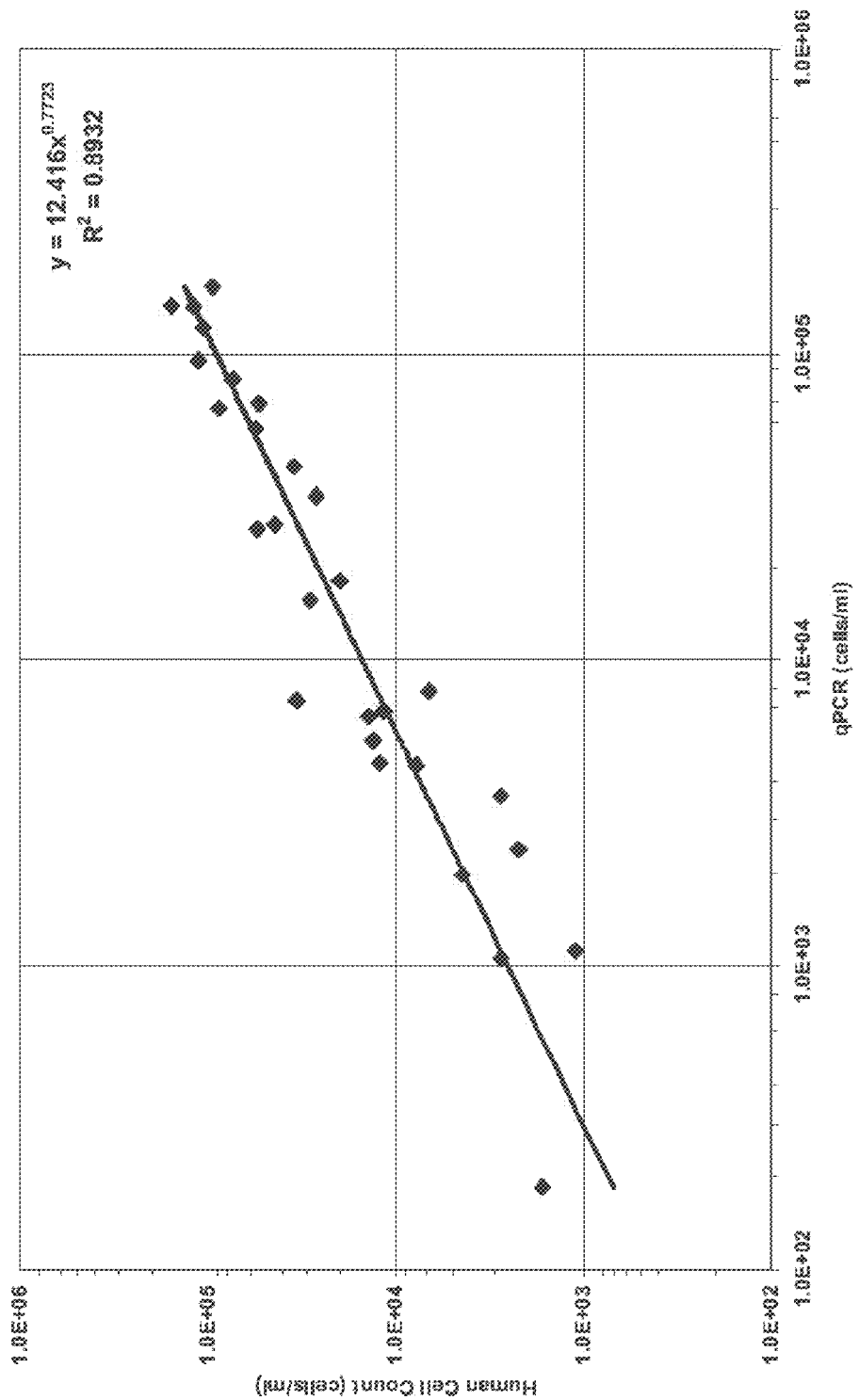
Figure 14:
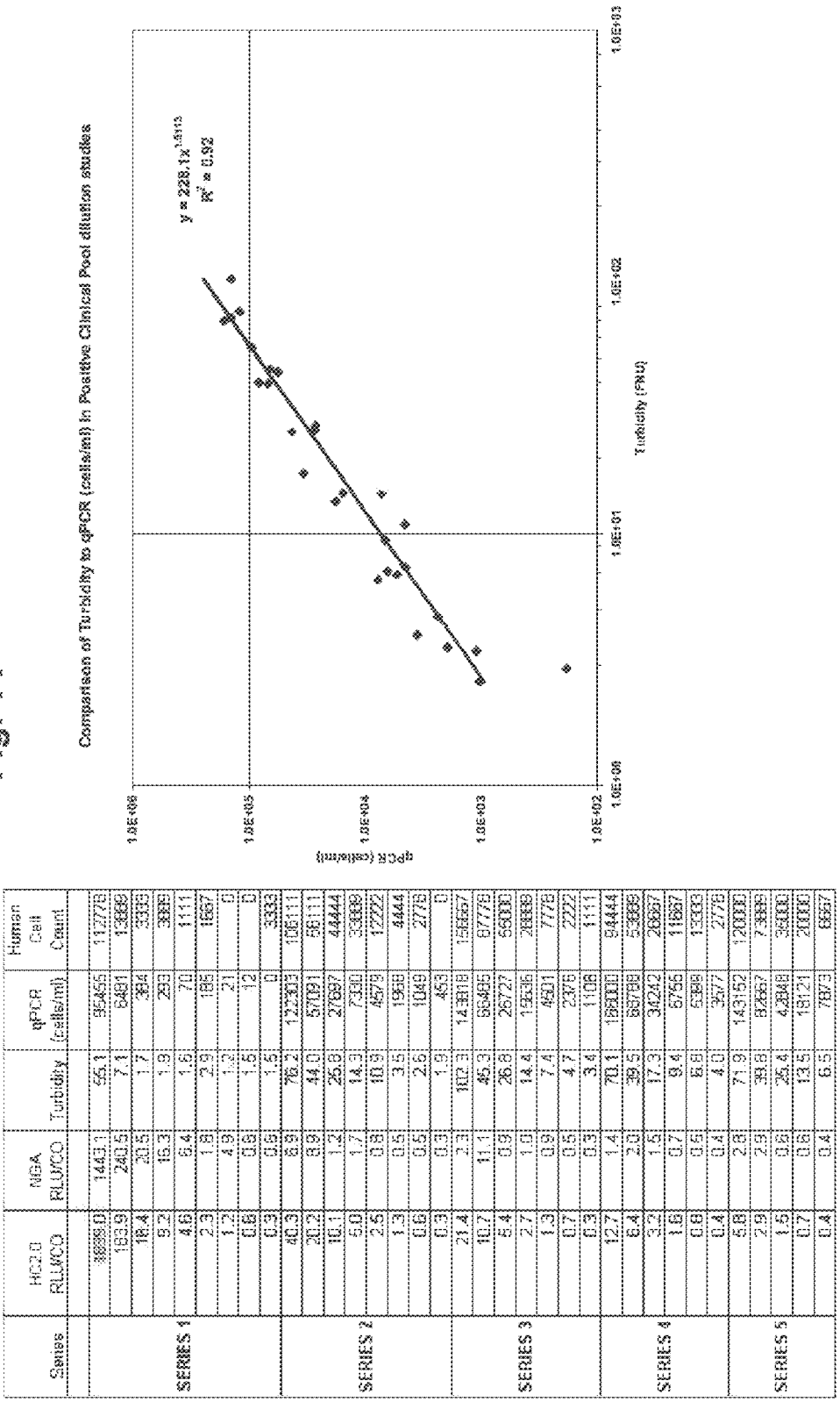

To further confirm the relationship and reduce the effects of sample variability 5 samples of cell density were serially diluted and the correlation between cell count and turbidity was found to be large with $r2>0.89$ for both turbidity or Beta-Globin versus cell count (FIGS. 12, 13, and 14). This evidence supports the notion that a cutoff could be defined that assures sample adequacy for 90-100% of the test population.

Figure 15:
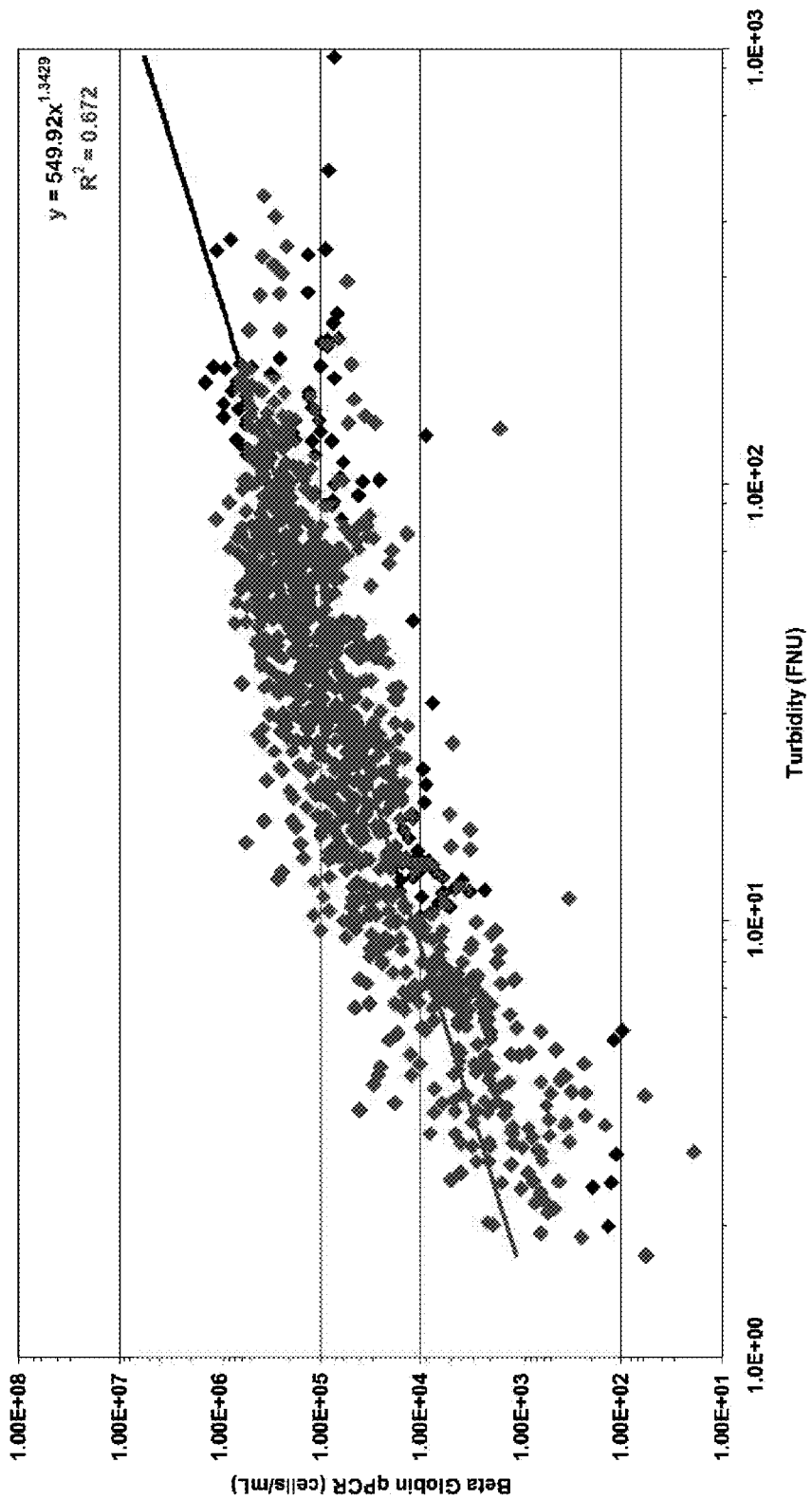
FIG. 15 shows the distribution of turbidity values of a population of cervical samples.
Figure 16:
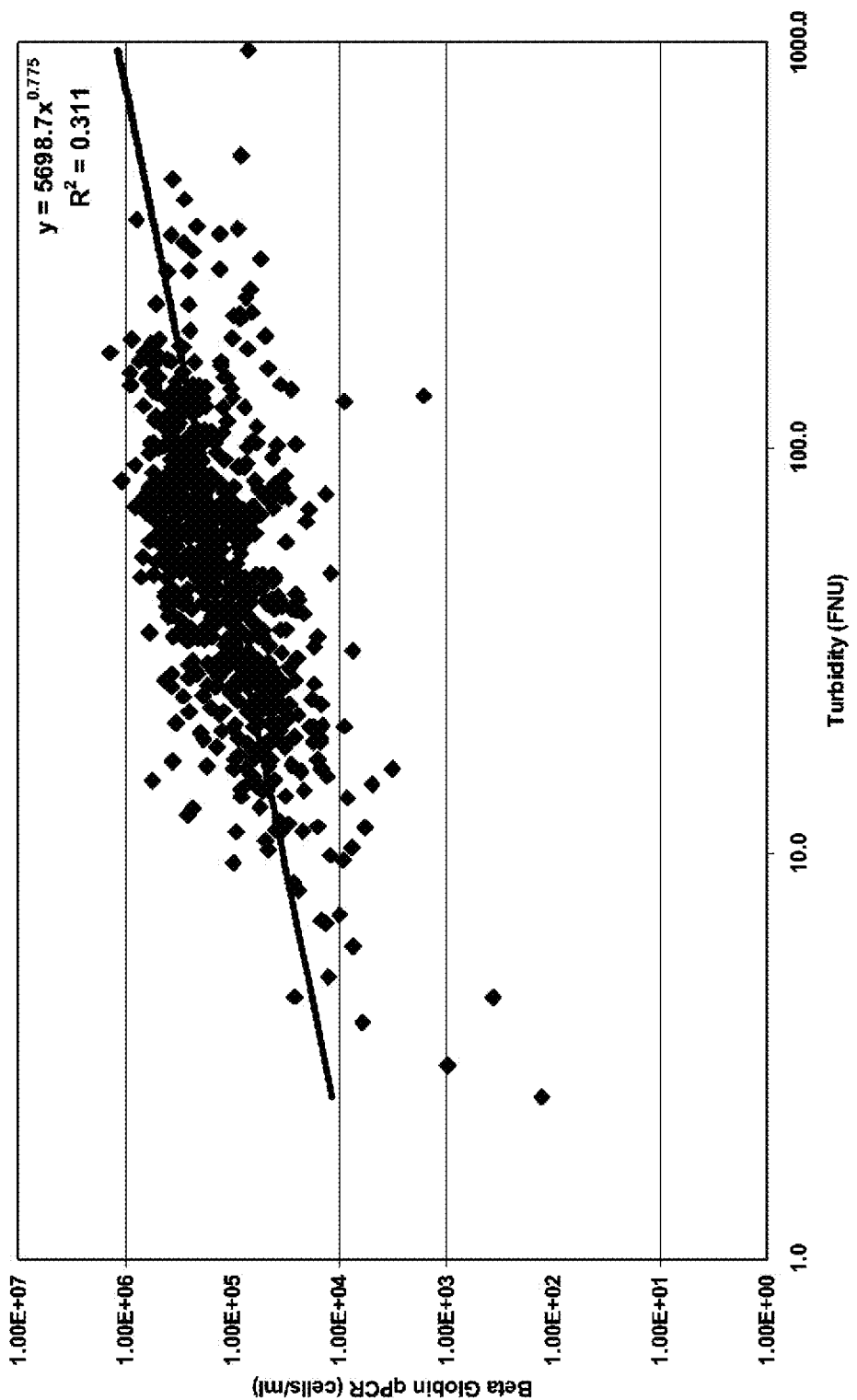
FIG. 16 illustrates the fraction of samples that would be retained or eliminated at a given turbidity cutoff.
Figure 17:
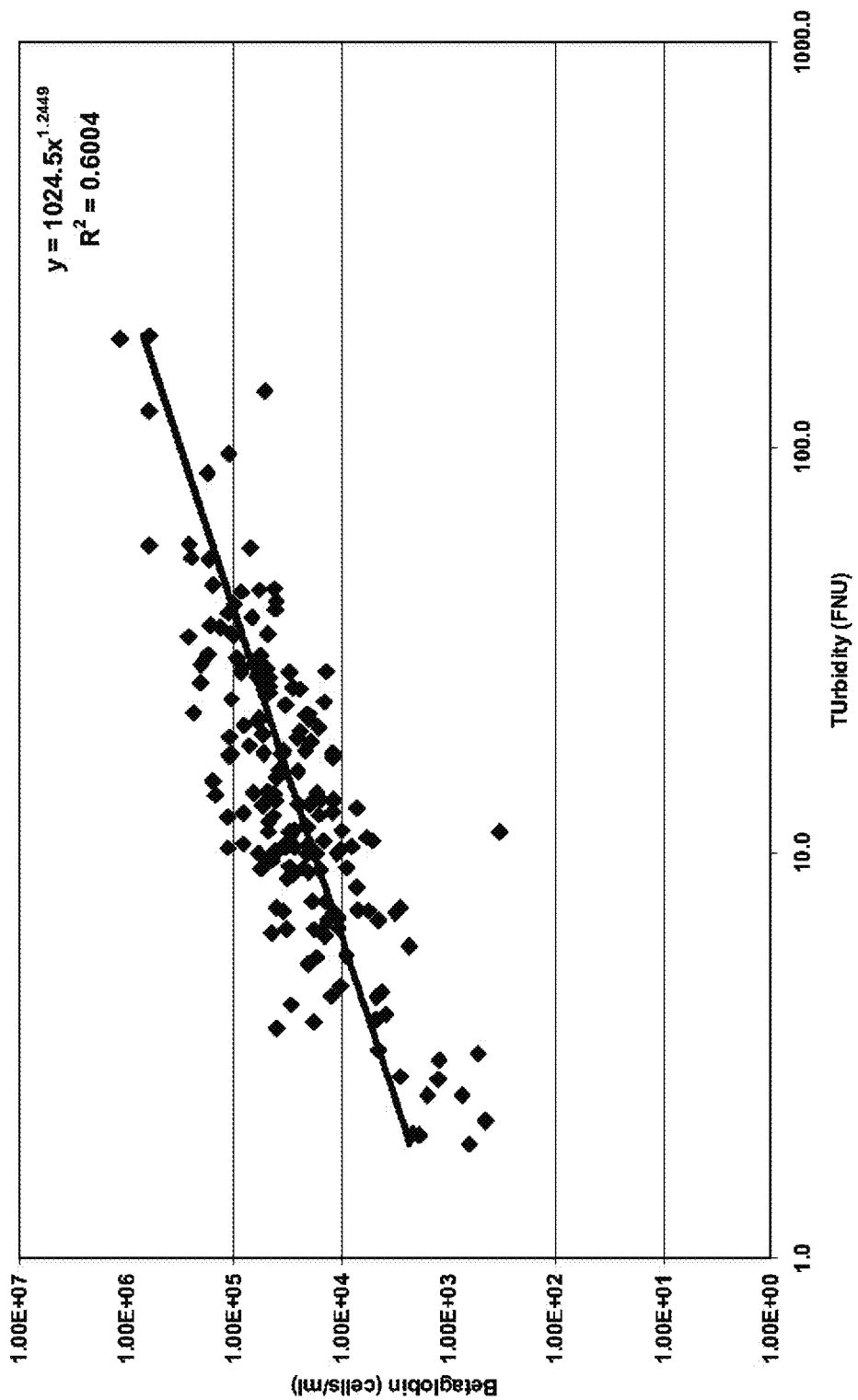
FIGS. 17-21 show comparison sample turbidity levels and cellularity determined by qPCR. Overall, this comparative study of turbidity values and the qPCR values for over 1000 clinical specimens in PreservCyt medium revealed a large correlation between the turbidity and cell density (cells/ml) ($R^2=0.7$).
Figure 18:
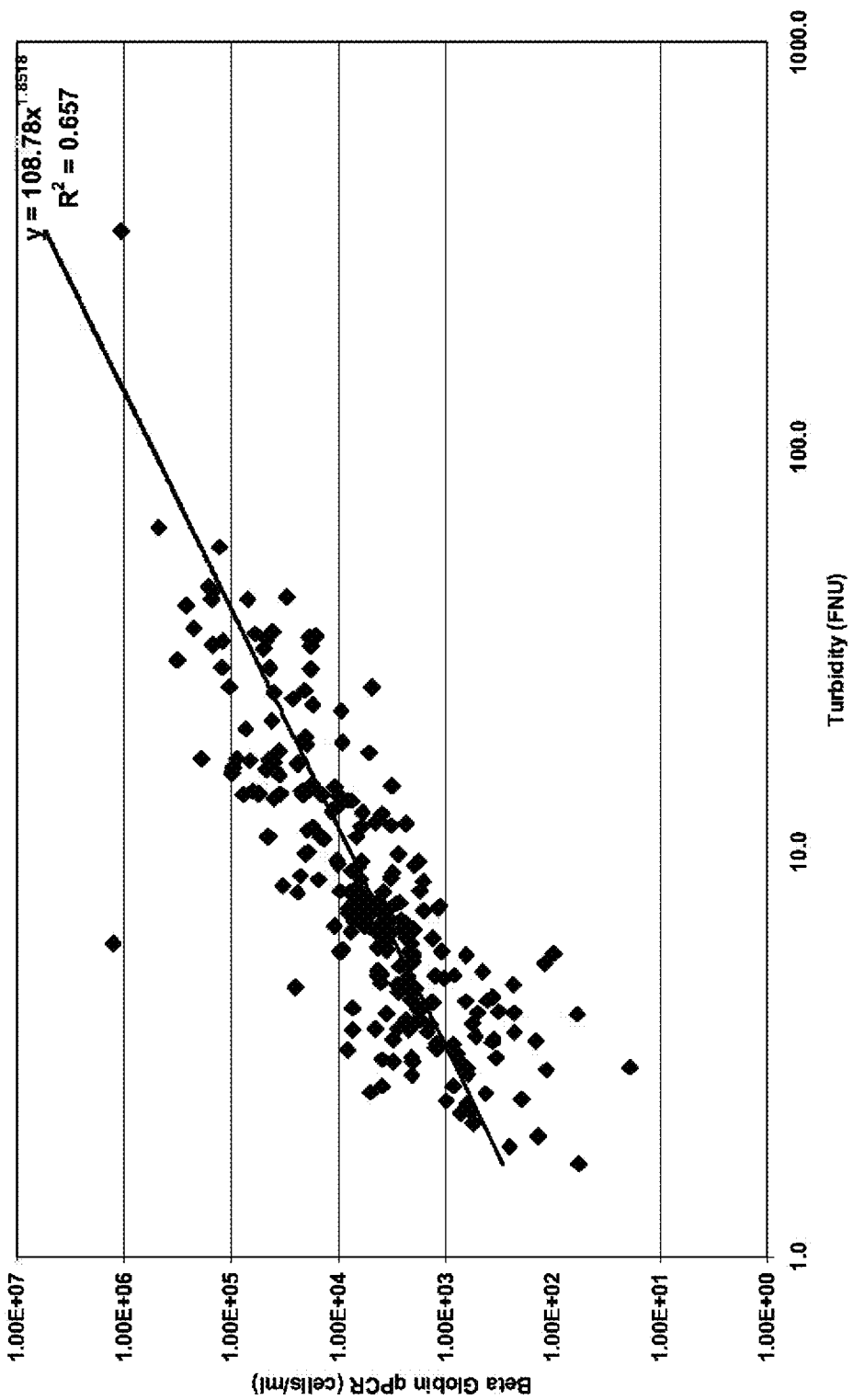

Referring now to FIG. 15, cellularity assessed by turbidity measurements and by qPCR values for over 1000 clinical specimens in PreservCyt medium revealed a large correlation between the turbidity and cell density (cells/ml) ($R^2=0.672$). Subsets of the data having different sample volumes are also shown individually: >4 ml volume (N=669, $R^2=0.311$) (FIG. 16); >2 ml and <4 ml volume (N=172, $R^2=0.6004$) (FIG. 17); and <2 ml volume (N=235, $R^2=0.657$) (FIG. 18).

Example 7

Turbidity of Samples Containing Bacterial and Human Cells

Figure 19:
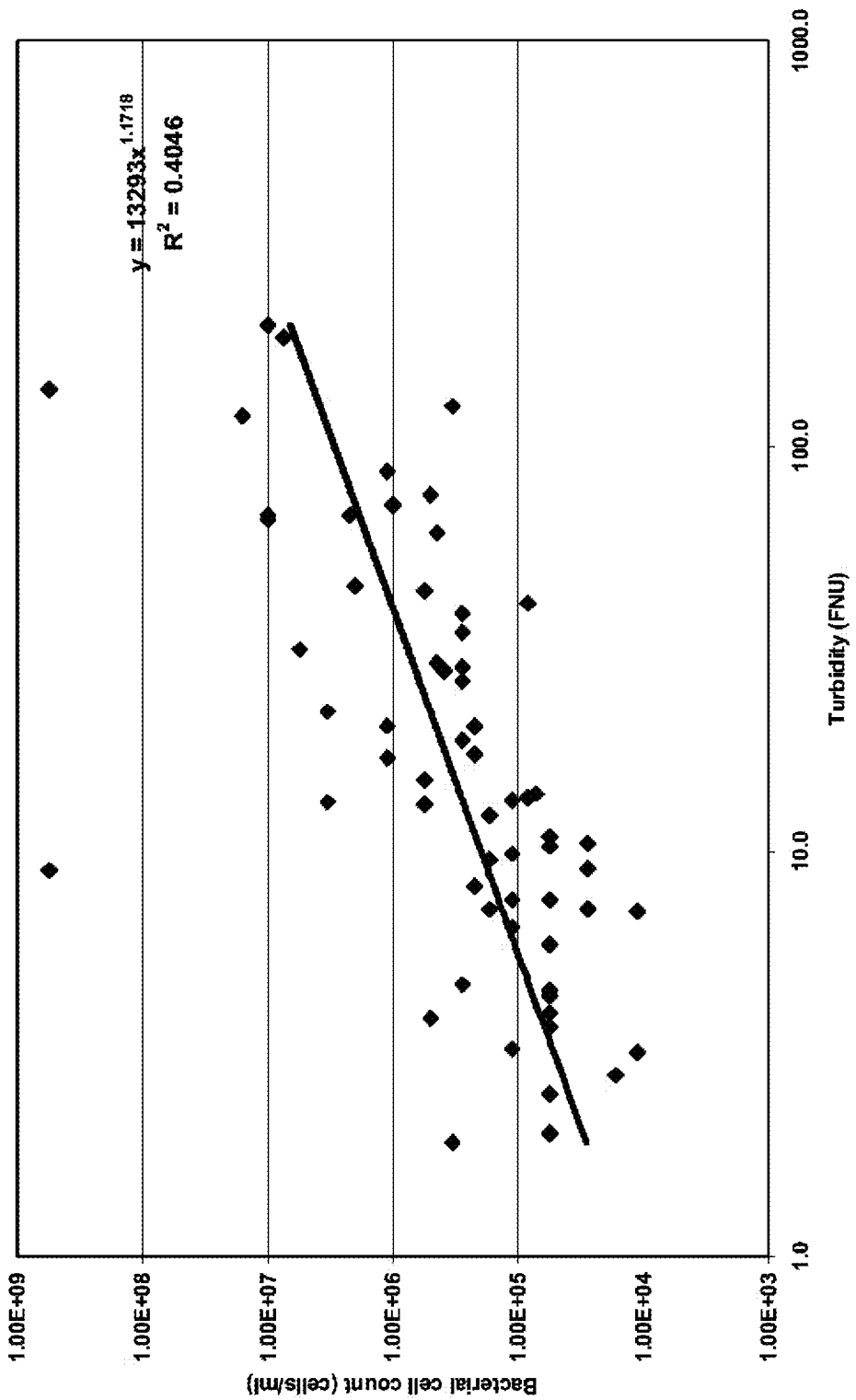
Figure 20:
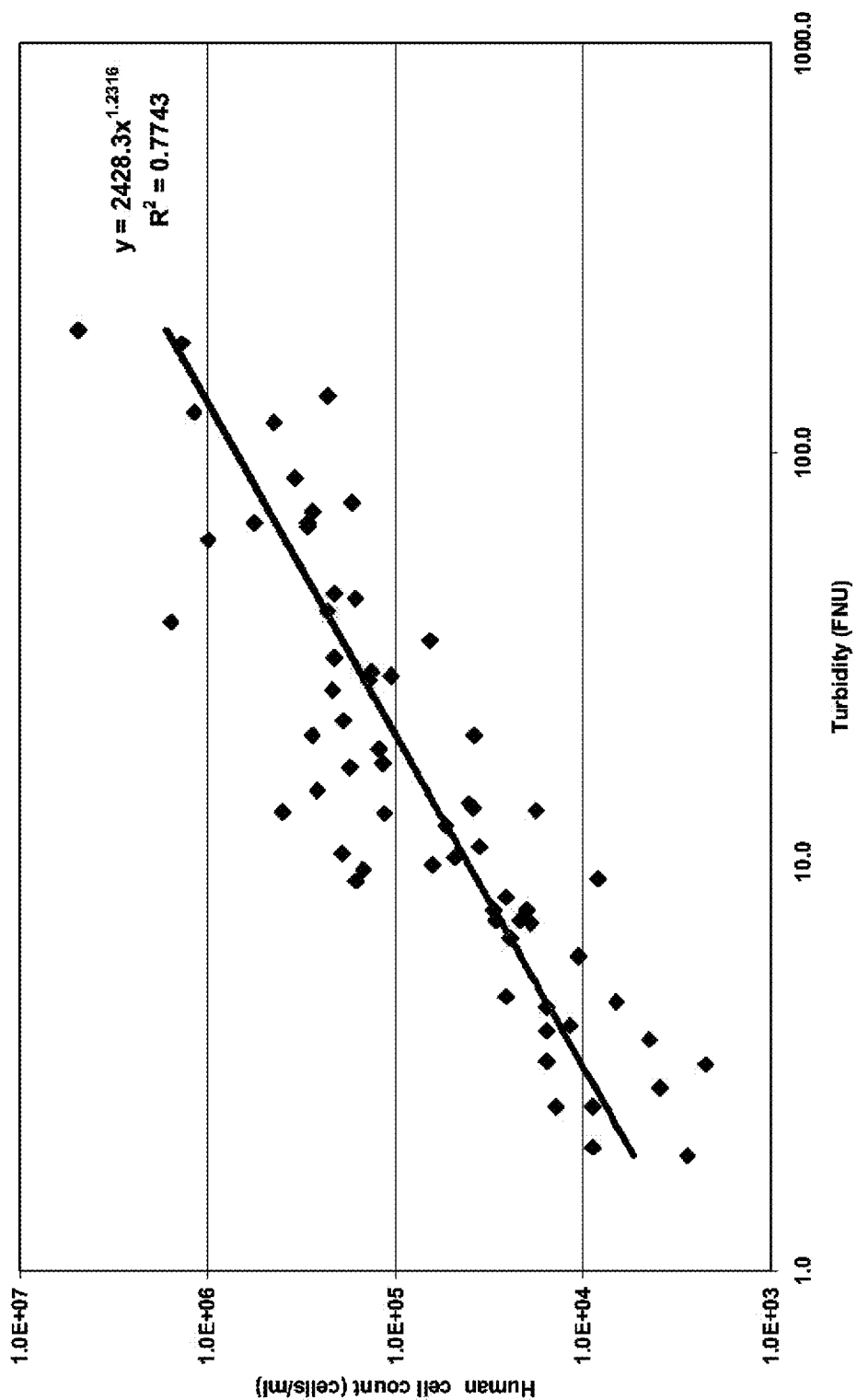
Figure 21:
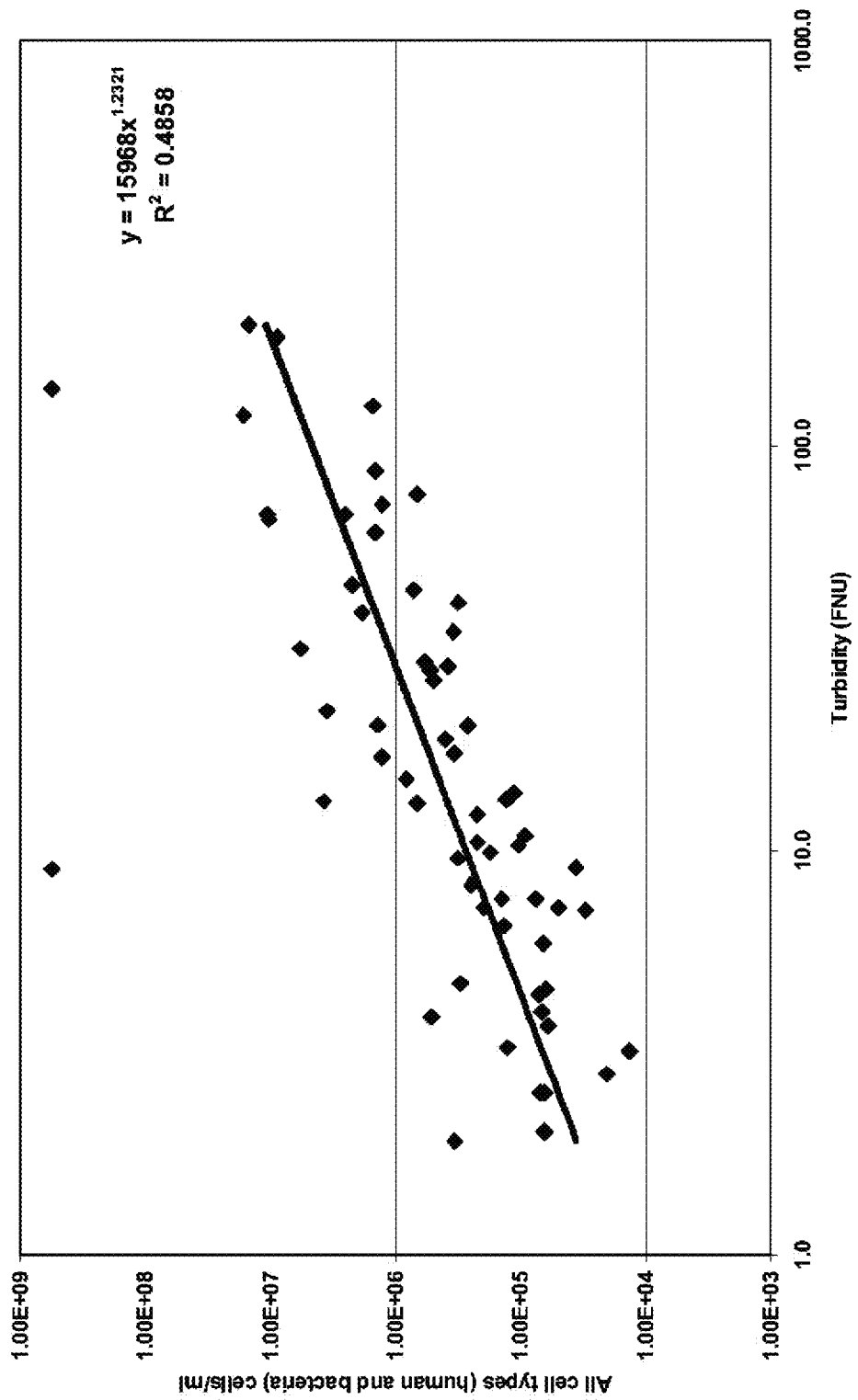

Since light scatter is a function of both the number and size of reflective particulate matter in a sample we tested whether turbidity methods could distinguish bacteria from the original swab from the human cells. Referring now to FIGS. 19, 20, and 21, using the Hach turbidity meter it is clear from the data below where the bacteria and human cells were counted separately that the size of the bacteria (approximately one tenth the size of the epithelial cells) do not dominate turbidity readings. Rather, the human cell turbidity readings dominate the bottom right of the line creating a boundary. Moreover, bacteria cell count correlation to turbidity is less than the human cell count correlation to turbidity. These results suggests that the dominate factor in turbidity measurement is the epithelial cell count.

Example 8

Distribution of Turbidity of Cervical Samples

Figure 22:
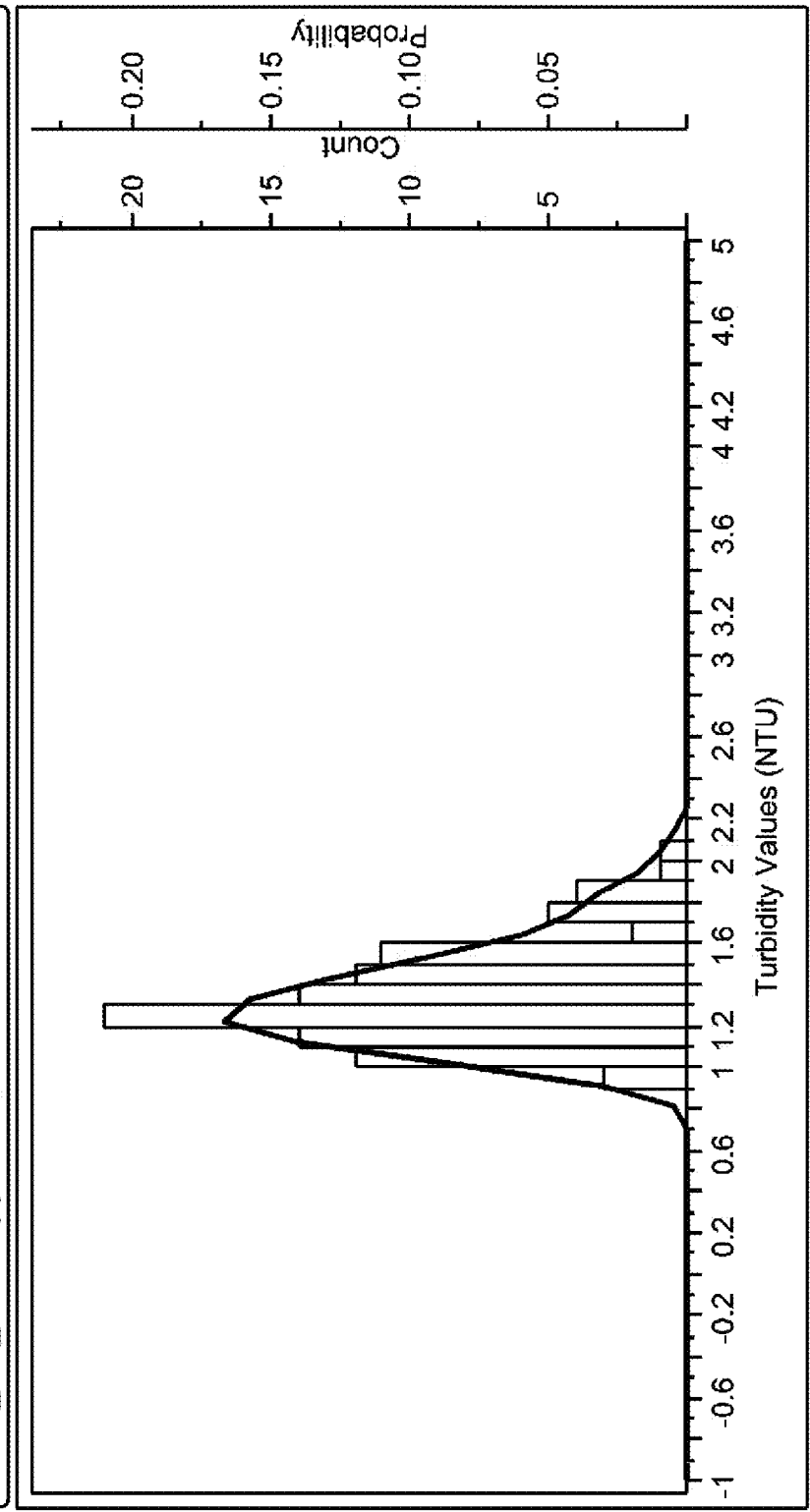
FIG. 22 shows the distribution of turbidity in samples from the Laurel, Md. population (further described in Example 4).
Figure 23:
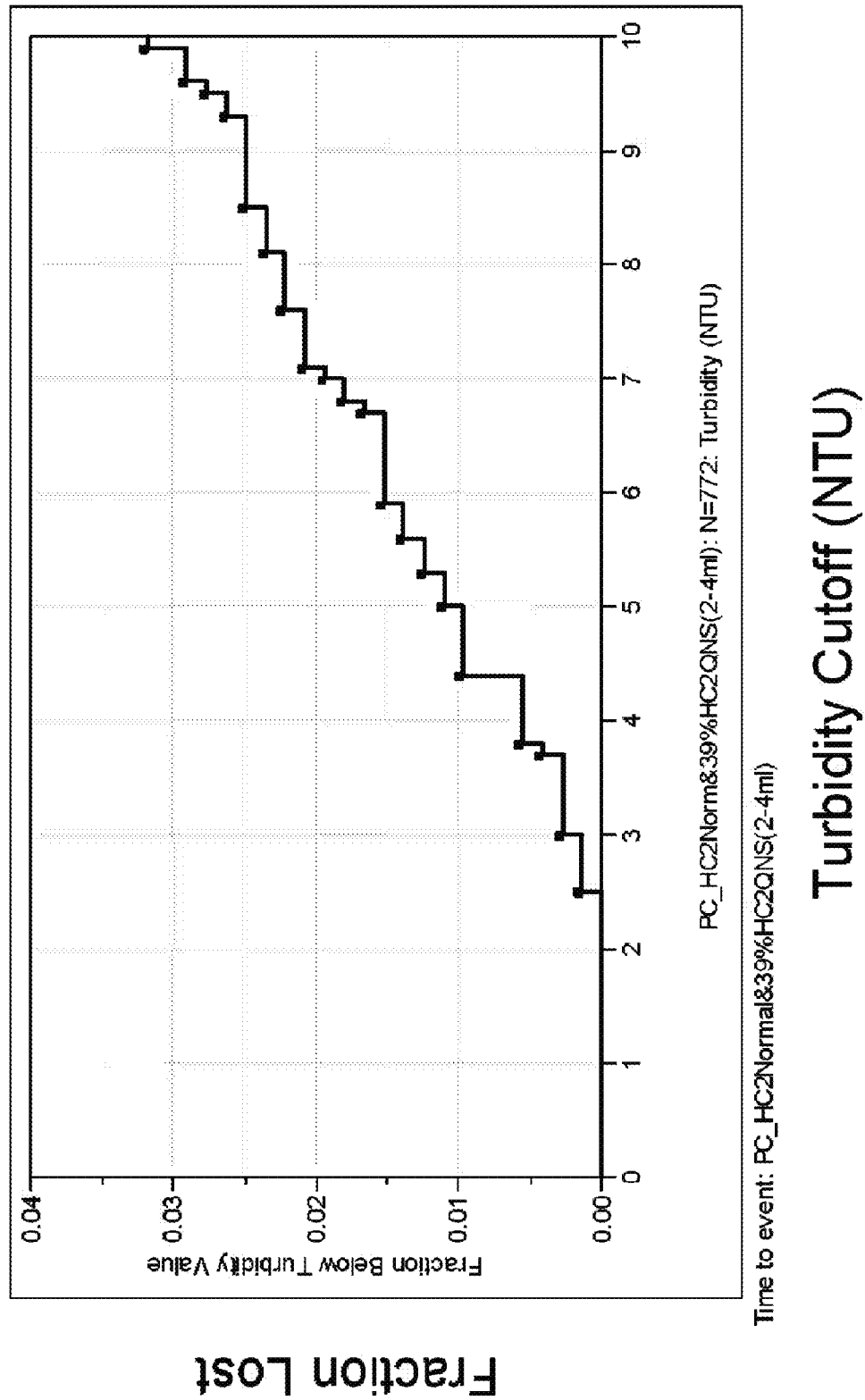
FIG. 23 shows the fraction of the Laurel, Md. population that would be considered inadequate based on its turbidity for a given sample adequacy cutoff decision.

FIG. 22 shows the distribution of turbidity in samples from the Laurel, Md. population (further described in Example 4 above). FIG. 23 shows the fraction of the Laurel, Md. population that would be considered inadequate based on it's turbidity for a given sample adequacy cutoff decision. For example, if a cutoff of 9 was selected then 2.5% of the population studied would be considered to have inadequate cellularity. Notice that the threshold of the meter is just sufficient that it could detect the entire population. For the HC2 HPV test, the anticipated CutOff is Between 2-20 FNU. Additional populations are analyzed by these methods to determine the representative nature of the sample and the clinical significance of the cutoff value for determining whether a sample is adequate.

Example 9

Figure 24:
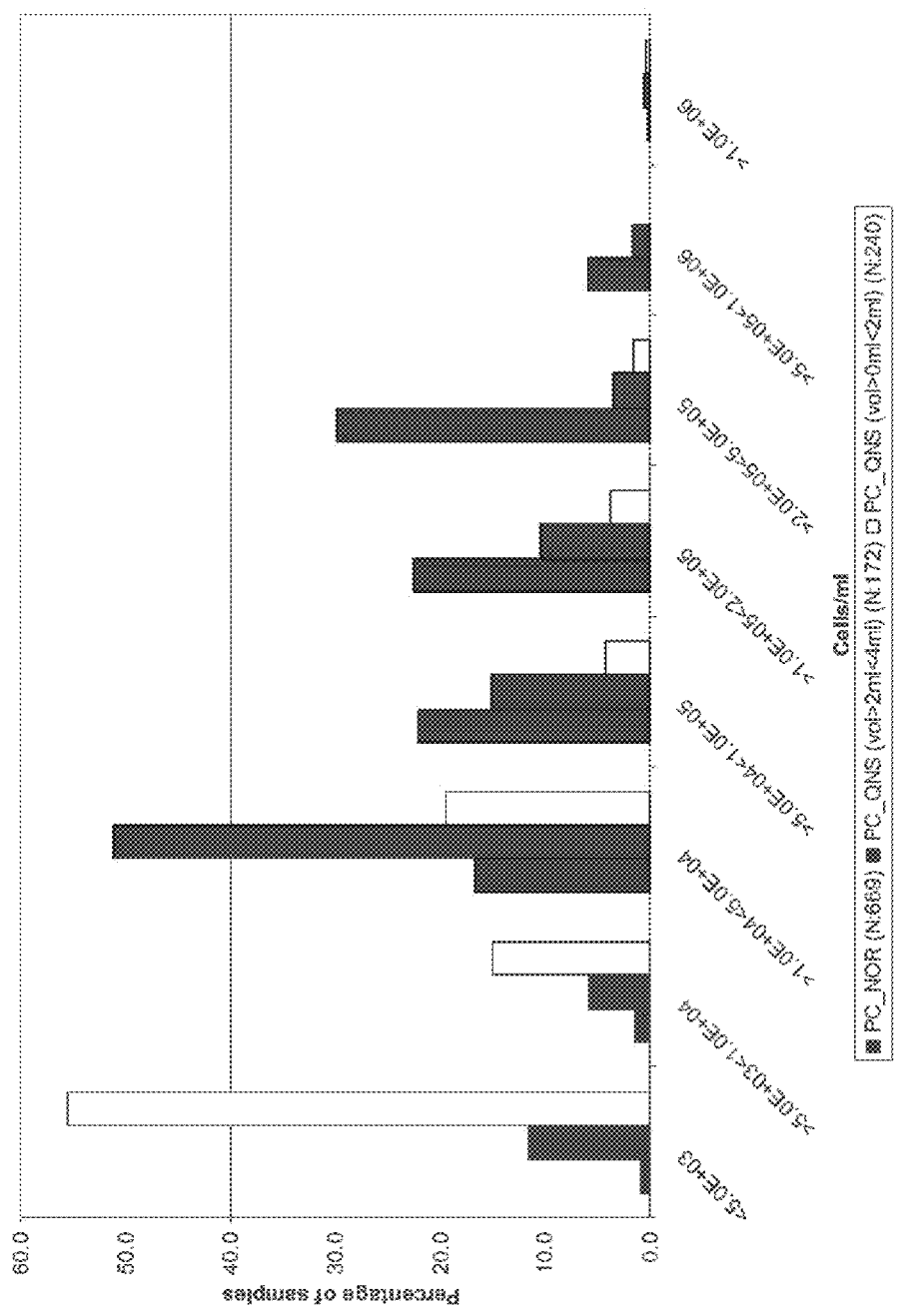
FIGS. 24-25 show the distribution of cellularity determined by qPCR and of turbidity values for clinical samples divided into subpopulations according to sample volume.
Figure 25:
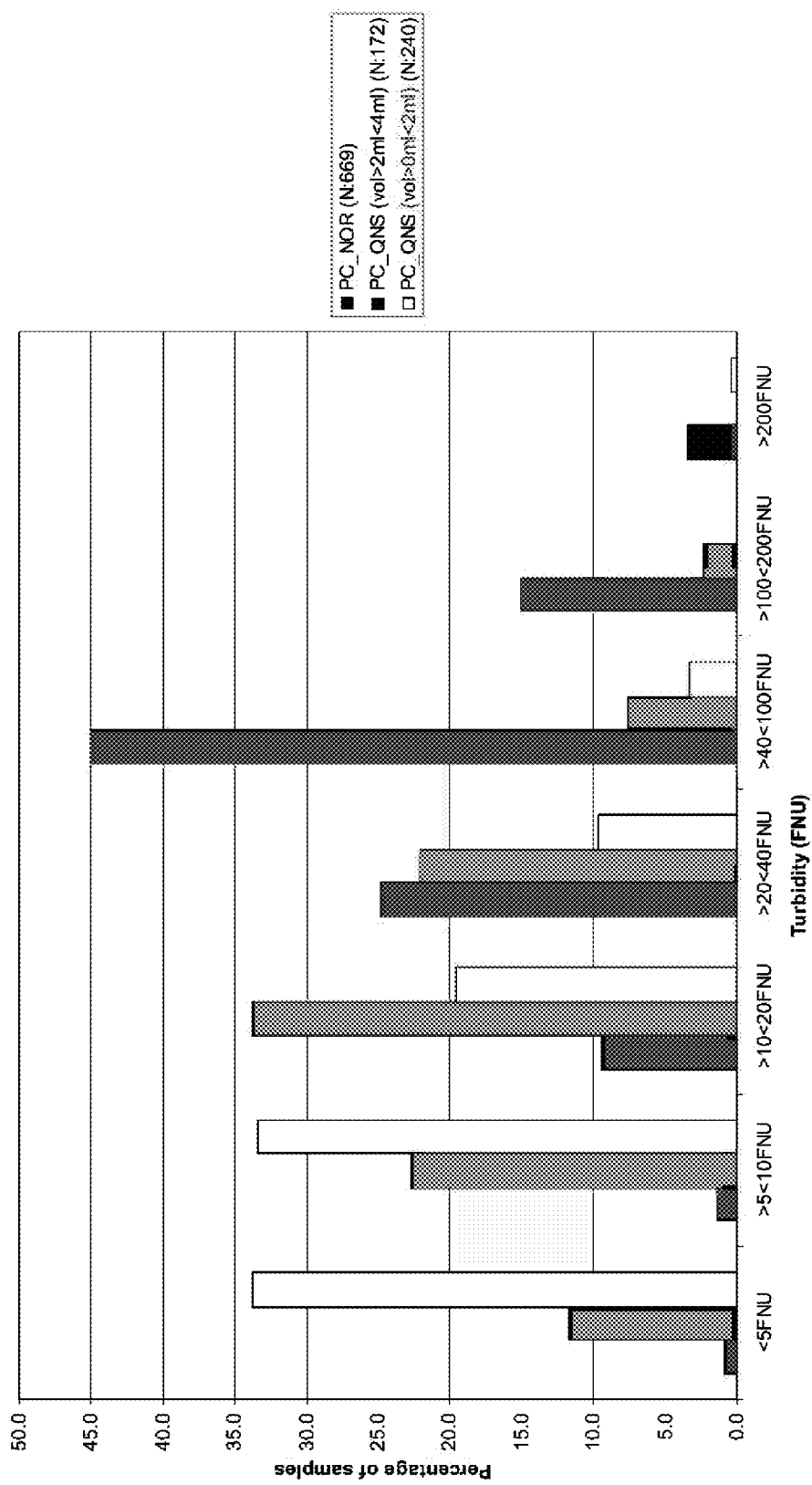
Figure 26:
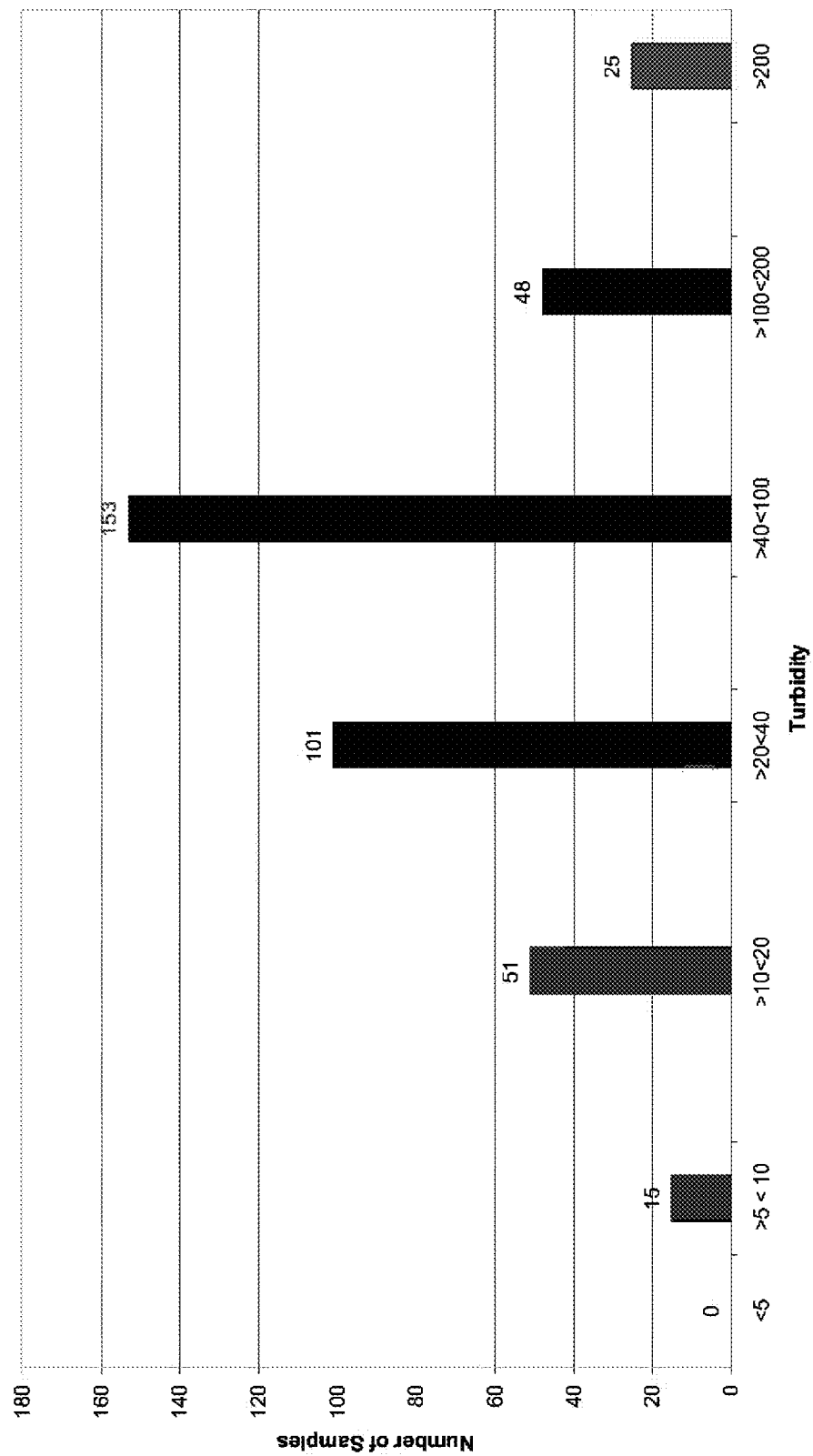
FIG. 26 shows the turbidity distribution for SurePath ("SP") samples.

Distribution of Turbidity and Cellularity Determined by qPCR for Cervical Samples FIGS. 24 and 25 show the distribution of turbidity and cellularity shows the percentage converted cell count distribution of samples analyzed by Beta Globin qPCR and with the Hach turbidity meter, respectively. The leftmost bars in each group correspond to samples having volume >5 ml (N:669); the center bars in each group correspond to samples having volume between 2 ml and 5 ml) (N:172); and the rightmost bars in each group correspond to samples having volume <2 ml (N:240). FIG. 26 shows the turbidity distribution for SurePath ("SP") samples.

Example 10

Determination of Turbidity Cutoff Value for Sample Adequacy

The one percentile minimum for turbidity of clinical samples in PreservCyt media was determined to be 7.4 NTU using an 8-channel detection system similar to the systems described in Example 3, above. The 99.7% confidence interval was 2 to 11.6 NTU. From analysis of turbidity of 800 PreservCyt samples, the cutoff values of 2, 7.5, and 11.6 would result in sample inadequacy for 0.125%, 1%, or 1.75%, respectively, of the population.

A further group of clinical samples is analyzed as described in the preceding paragraph, resulting in determination with greater accuracy the fraction of the population that would be determined to be less than a given turbidity cutoff value.

Example 11

Determination of the Sufficiency Threshold for the QIAGEN HR HPV DNA Test®

As discussed above, a sample can be inadequate when the number of cells in a sample is insufficient to permit detection of a signature of HPV infection (such as HPV DNA). The particular assay employed dictates the amount of sample required for positive detection; thus, as assay sensitivity improves, sample adequacy requires less and less sample. Accordingly, a sufficiency threshold can be established with respect to a particular assay. Additionally, patient-specific and sample-specific characteristics (such contaminants and undesired materials that contribute to turbidity) and other sources of variability are expected to contribute to variance in the sufficient number of cells for detection. Accordingly, an adequacy "threshold" can be expressed as a probabilistic relationship between amounts of sample and the probability that the sample is sufficient for detection of a true positive.

This example describes the determination of a sufficiency threshold for the QIAGEN HR HPV DNA Test® (also referred to as the HC2 assay). Cell samples from HPV-infected individuals are obtained. The cell content of the samples is determined by cell counting, by quantification of genomic DNA, and by turbidity measurement (all as described in the Examples above). Serial dilutions of the known numbers of cells are then individually tested to establish the sample concentration at which the true HPV positive clinical sample yields a false negative result. Samples independently collected from multiple individuals are tested in this manner, in sufficient numbers to establish a statistically validated correlation between the sample concentration and probability of detection of a true positive HPV infection. Thresholds are then established at which defined sensitivity is obtained, such as 90%, 95%, 97%, 98%, 99%, 99.5%, 99.9%, 99.95%, or 99.99% probability that a sample concentration is adequate for a true positive HPV infection to be detected.

Example 11

Methods of Using Determined Sample Adequacy to Save Reagents or Provide Sample Assurance Methods and machines described herein may be used to determine whether a sample contains sufficient cellular or other material to be considered adequate to give sensitivity above a determined threshold for a given test. As noted above, for some tests, a positive result may be obtained and be meaningful even though a sample is inadequate to provide confidence in a negative result. If an inadequate sample is not tested, reagents may be saved, potentially reducing costs. A default decision may be made in advance that samples only above some threshold level of adequacy will be tested. Alternatively or in addition to a pre-set default criterion, an indicator may be displayed to a decision maker who would then be given the option to determine whether an inadequate sample should be tested (potentially overriding the default).

Additionally, an indicator of sample adequacy may be provided to together with test results. Sample adequacy may be indicated as two or more discrete values (e.g., "yes," "borderline," or "no"). For example, sample adequacy may be given as a reliability measure reflecting the statistical probability that a positive result would have been detected given the determined level of sample adequacy.

Additionally, sample adequacy may be reported (for example, as individual values or in summary or aggregate form) to individuals responsible for collecting samples or other persons involved including supervisors, managers, trainers, etc. Sample adequacy information can potentially provide feedback to these individuals that can reveal a need for appropriate corrective action.

Example 12

Protocol for HACH 2100AN Turbidity Meter

In the examples described herein, turbidity measurements using the HACH 2100AN turbidity meter were performed essentially according to the following protocol:

Turn power on
Open "collect" program on the computer
From top menu select "Instruments" then "open"
Open "HACH 2100AN"
Choose a data destination
Excel work sheet with sample turbidity template opens
From top menu select "Instruments" then select "Commands"
From the "command menu" select "30 read at 1 second interval"
Enter Sample ID number by scanning the barcode of the sample
Pipette 1.5 to 2 mL sample into a polystyrene or PETG tube.
Vortex sample for 2 seconds
Place the tube in the HACH meter sample slot
Select send from the "command menu"
When Finished hit the "stop" button located on the top menu
'Select "instrument" then "exit"

Example 13

Protocol for 8-Channel Detection System

In the examples described herein, turbidity measurements using an 8-channel turbidity meter were performed essentially according to the following protocol:

Open SAC-UI (Sample Adequacy Control-User Interface)—This opens "QIAGEN SAC interface Simulator".

The SAC UI has four command options. The $1^{st}$ command option is "Operation Commands" $2^{nd}$ "Diagnostic Commands" $3^{rd}$ "Calibration Commands" $4^{th}$ "Manufactures Commands". The Operations Command allows the user to change the user mode and take turbidity measurements. The Calibration commands allow users to create or upload calibration data.

From the Operation Commands—select MD-Set Mode—Set mode to "M" manufacture this mode allows the user to create or upload calibration data.

Scroll down to "Calibration Commands" then Select "CD-Upload Calibration" this will upload Calibration data.

Go to "Operation Commands" Set Mode to "O"—Operator mode:—This will disable access to calibration data. It will also prevent accidentally changing the calibration of the Unit.

Now the system is ready to read turbidity of samples. Load Samples in an 8-channel sample holder with a minimum volume of 1.5 ml.

"Operation Commands" has two important icons to read and display turbidity value. "BG-Begin Read" sends the signal for the turbidity to be read. "SA-Acquire Sample" sends the signal for the turbidity value to be displayed. Click on "SA-Acquire Sample" in order to see the turbidity value.

$1^{st}$-BG-Begin Read
$2^{nd}$-SA-Acquire Sample

Once the turbidity reading is complete the error box will display "no error" on both BG-Begin Read and SA-Acquire Sample column.

The "Results box" displays the turbidity value for each channel starting with channel one.

Results [chnl 1, chnl 2, - - - chnl 7, chnl 8]

Turbidity value is displayed in 3 decimal places. The value displayed is NTU×10

Example, If the value displayed on channel one is '053' the turbidity is 5.3 NTU. If the value on Channel one is '235' the turbidity is 23.5 NTU.

Example 14

Protocol for Counting Cells

In the examples described herein, cell counting was performed essentially according to the following protocol:

Shake sample using mechanical mixer for 30 seconds at 4000 rpm

Pipette 50 μL sample in to 1.5 mL centrifuge tube (mix thoroughly before taking sample)

Add 5 uL Cyto-stain dye, mix sample.

Incubate at room temperature for 30 minutes

Clean Hemacytometer and cover Slip using DI water and 70% alcohol

Carefully place cover slip on Hemocytometer

Pipette 11 uL sample and dye mix in to the chamber the sample will disperse evenly by capillary action. Make sure you do not move the cover slip once you have added a sample; this will disturb even distribution of cells.

Count cells overlapping Top and left edge of the square (Omit cells overlapping bottom and right border of the square—this will eliminate counting the same cell multiple times.)

If there are less than 50 cells or more than 200 cells per 1 $mm^2$ area adjust the dilution.

Count at least five 1 $mm^2$ area squares. The Four squares at each corner and center square.

For a low cellular sample count all 18 squares.

Calculations

Count number of cells within each primary square

Divide by the number of primary squares counted which gives the average cell count Multiply the average number of cells by $10^4$ to obtain the number of cells per mL.

If the sample has been diluted multiply the value with the dilution factor.

Example 15

QIAamp Extraction Protocol (QIA96 MinElute Protocol—for DNA Isolation)

In the examples described herein, extraction of DNA from cells was performed essentially according to the following protocol:

When kit is new, prepare Buffer AW2 by adding 30 mL of ethanol to the reagent bottle (comes with 13 mL pre-aliquotted).

Mark the Buffer AW2 bottle to show EtOH has been added.

Store at room temperature, stable for one year.

Bring all samples and reagents ATL, AL, AVE, AW2 to room temperature.

Turn on deep well plate heaters and equilibrate to 56 C. and 70 C.

Mix enough Buffer ATL with Proteinase K at 80:20 ratio to add 100 uL to each sample. See calculator below. Add 100 uL Buffer ATL/PK mix to each well of S-block.

Add 250 uL of sample to well on the S-Block+++

Shake on plate shaker at 1100 rpm for 15 sec.

Incubate in 56 C. in deep well plate heater for 30 minutes.

During this incubation add cRNAAVE (see below) to buffer AL according to calculations below.

Remove S-Block from deep well plate heater

Add 250 uL Buffer AL with cRNA to each well of S-block. shake on plate shaker at 1100 rpm for 15 sec.

Incubate in 70 C. in deep well plate heater for 15 minutes.

While incubating, add 900 ul of water to balance S-block in the same wells as sample wells in your S block Add 300 uL 100% ethanol to each sample.

Cover S-block and Shake at 1000 rpm for 15 seconds, with brief pause@every 5 seconds (WATCH FOR SPLASHING)

Incubate at room temp for 5 minutes.

For each sample, label a plate map with position on the QIA96 plate.

Sblock: Use a multichannel pipette to transfer lysate from the S-block to the QIA96 plate on a NEW S-Block. The same S-block can be used, but as a precaution for contamination, a new S-block is used.

Centrifuge for 1 min@3000 rpm; Use S-block under QIA96 plate to catch waste

Dump S-Block and blot

Remove 150 ul from balance S-Block

Shake buffer AW2 well. Add 750 uL Buffer AW2 into the wells of the QIA 96 plate. Place on S-Block Centrifuge for 1 min @ 3000 rpm Dump S-Block and blot Add 750 uL 100% EtOH into the QIA 96 plate Centrifuge for 1 min@3000 rpm Dump S-Block and blot Centrifuge for an additional 3 minutes Place a kimwipe (or Hyb plate) under QIA96 Plate, incubate at 56 C. for 5 min in deep-well heater to further dry the membrane, Place QIA96 block on elution plate Add 100 uL Buffer AVE directly to the membrane, Add 35 uL Top-E fluid to the wells; incubate at RT for 5 minutes Add 135 ul of water to "balance" elution plate Spin for 1 min.@3000 rpm.

Eluate in tube should be aliquoted to multiple plates at 10 ul and stored at −20 C. (or 4 oc if used the same day)

Buffer AL with cRNA 310 ug cRNA is provided lyophilized.

To make solution cRNAAVE (carrier RNA in buffer AVE at 1 ug/uL): Add 330 uL Buffer AVE to this tube, mix gently but thoroughly, then aliquot to individual tubes to be stored at −20° C.

Buffer AL with cRNA is then made as follows: per sample, mix 300 microliters of buffer AL and 1.5 microliters of cRNAAVE. Example: for 96 samples, mix 28800 microliters of buffer AL and 144 microliters of cRNAAVE.

Example 16 qPCR Assay Protocol

In the examples described herein, qPCR was performed essentially according to the following protocol:

Cycle 1

95° C. for 5 min

Cycle 2 (45×)

95° C. for 15 secs

52° C. for 30 secs

72° C. for 30 secs

Setup

In an amplicon-free room remove the PCR reaction components from the −20° C. freezer to thaw completely.

Allow samples, Genomic DNA, and reagents to thaw completely at room temperature.

Make a serial dilution of Genomic DNA standard curve, (Vortex for 10 seconds before each aliquot).

Make a plate layout as shown below—There can be 80 samples per PCR plate.

Plate Layout:

| | 1 | 2 | 3 | 4 | 5 | 6 | 7 | 8 | 9 | 10 | 11 | 12 |
|---|---|---|---|---|---|---|---|---|---|---|---|---|
| A | STD-1 | STD-1 | S1 | S9 | | | | | | | | |
| B | STD-2 | STD-2 | S2 | S10 | | | | | | | | |
| C | STD-3 | STD-3 | S3 | S11 | | | | | | | | |
| D | STD-4 | STD-4 | S4 | S12 | | | | | | | | |
| E | STD-5 | STD-5 | S5 | S13 | | | | | | | | |
| F | STD-6 | STD-6 | S6 | S14 | | | | | | | | |
| G | STD-7 | STD-7 | S7 | S15 | | | | | | | | |
| H | NTC | NTC | S8 | S16 | | | | | | | | |

In a clean room make a PCR Master as shown below. The total volume is the vol. times the number of reactions that are needed. An example is shown below.

qPCR Master Mix

Using a repeat pipette add 45 μl of master mix to each well as indicated by the plate layout Vortex the standards for 10 seconds and add 5 μl to the designated wells.

Vortex the isolated DNA from Clinical samples for 10 seconds and add 5 ul to the designated wells (PreservCyt samples).

Add 5 ul of MBG water to the Negative Control (NTC) designated wells.

For Strategene PCR machine, open software on the computer. Follow the manual to setup a plate layout and appropriate condition, run the assay (The assay will takes 1 hour and 41 minutes).

After the run, click to save the file

Acceptance Criteria

The Slope of the standard curve is in the range of −2.5 to −3.8.

The $R^2$ for the standard curve is equal to or greater than 0.90.

The $C_T$ for the negative controls in the plate is greater than 40 cycles.

Example 17

Background Turbidity of Blank Samples

When trying to determine the threshold of the turbidity meter 100 blank 2 mL PC media filled 5 mL polystyrene tubes with no cervical sample were measured as blanks. There is 99.5% confidence level that the blanks would not exceed a turbidity of 2.04 NTU. Limit of detection relative to the gold standard cell count can be readily determined for a particular turbidity meter.

While the invention has been described by way of examples and preferred embodiments, it is understood that the words which have been used herein are words of description, rather than words of limitation. Changes may be made, within the purview of the appended claims, without departing from the scope and spirit of the invention in its broader aspects. Although the invention has been described herein with reference to particular means, materials, and embodiments, it is understood that the invention is not limited to the particulars disclosed. The invention extends to all equivalent structures, means, and uses which are within the scope of the appended claims.

What is claimed is:

1. An automated method for assuring sample adequacy, the method comprising:

providing a sample in a testing container;

activating an illumination source to pass an illumination beam through the testing container and into the sample, wherein the illumination beam travels upwards in a vertical direction as it passes through the testing container;

detecting an intensity of an emitted beam, the emitted beam comprising at least a portion of the illumination beam that has been scattered by the sample;

generating a reference beam by transmitting a portion of the illumination beam that is between the illumination source and the testing container along a reference beam path located below and outside the testing container;

measuring an intensity of the reference beam using a reference detector;

generating a sample turbidity measurement based on the intensity of the emitted beam; and determining, based on the sample turbidity measurement, an adequacy of the sample to provide accurate results in a primary test of the sample;

conducting the primary test of the sample to obtain a primary test result;

evaluating the primary test result to determine whether the primary test result is a negative primary test result; and reporting the negative primary test result only if the sample was determined to be adequate to provide accurate results in the primary test of the sample;

wherein the testing container is one of a plurality of testing containers in a tube unit, the tube unit comprising a frame extending horizontally along a longitudinal axis with the plurality of testing containers connected to the frame and arranged in a line along the longitudinal axis, and wherein each one of the plurality of testing containers extends downward in the vertical direction below the frame; and wherein the emitted beam is detected by a sample detector positioned along a vertical extent of the testing container, wherein the sample detector is positioned at the end of an emitted beam path, and wherein the emitted beam path extends in a plane that is perpendicular to the vertical direction and is oriented at a non-perpendicular angle with respect to the longitudinal axis, to thereby reduce the likelihood that the emitted beam will pass through a scratched portion of the testing container.

2. The automated method for assuring sample adequacy of claim 1, wherein determining the adequacy of the sample comprises comparing the sample turbidity measurement with one or more predetermined criteria.

3. The automated method for assuring sample adequacy of claim 1, wherein the sample turbidity measurement correlates to the number of proteins, nucleic acids, cells or viruses in the sample.

4. The automated method for assuring sample adequacy of claim 1, wherein the sample turbidity measurement comprises an estimation of a number of cells in the sample, and determining the adequacy of the sample comprises comparing the estimation of the number of cells in the sample to a minimum number of cells.

5. The automated method for assuring sample adequacy of claim 1, further comprising storing one or more sample adequacy results and analyzing the one or more stored sample adequacy results to identify at least one of; sample gathering errors, sample handling errors, sample processing errors, sample adequacy measurement errors, sample adequacy measurement calibration requirements, or a combination of the preceding.

6. The automated method for assuring sample adequacy of claim 1, further comprising providing an indicator of the adequacy of the sample to an operator.

7. The automated method for assuring sample adequacy of claim 6, further comprising allowing a decision maker to determine whether an inadequate sample should be tested if the sample was determined not to be adequate.

8. The automated method for assuring sample adequacy of claim 1, wherein conducting the primary test is performed after determining the adequacy of the sample.

9. The automated method for assuring sample adequacy of claim 1, wherein the sample comprises a human cervical sample and the primary test is a Human Papillomavirus screening test.

10. The automated method for assuring sample adequacy of claim 1, further comprising controlling the illumination source to regulate an intensity of the illumination beam based on the intensity of the reference beam.

11. The automated method for assuring sample adequacy of claim 1, further comprising using the reference beam to determine whether an intensity of the illumination beam is within an acceptable intensity range.

12. The automated method for assuring sample adequacy of claim 1, further comprising homogenizing the sample prior to or while detecting the intensity of the emitted beam.

13. The automated method for assuring sample adequacy of claim 12, wherein homogenizing the sample comprises mixing the sample using an orbital agitator, a linear agitator, a mixer comprising a paddle, a robotic arm that moves the testing container in a fashion that homogenizes the sample, aspiration by a pipettor, or dispensing by a pipettor.

14. The automated method for assuring sample adequacy of claim 1, wherein the illumination beam comprises monochromatic light.

15. The automated method for assuring sample adequacy of claim 1, wherein the emitted beam passes through a protected portion of the testing container.

16. The automated method for assuring sample adequacy of claim 15, wherein the testing container comprises a cylindrical tube, the illumination beam passes through an end of the cylindrical tube, and the emitted beam passes through a side of the cylindrical tube.

17. The automated method for assuring sample adequacy of claim 1, wherein detecting the intensity of the emitted beam comprises measuring the emitted beam at multiple detector angles and algorithmically combining the measurements at multiple detector angles to yield a single turbidity reading.

\* \* \* \* \*